(12) United States Patent
Reiley et al.

(10) Patent No.: US 8,715,362 B2
(45) Date of Patent: May 6, 2014

(54) ANKLE REPLACEMENT SYSTEM

(75) Inventors: Mark A. Reiley, Piedmont, CA (US);
Louis E. Greenberg, Boulder, CO (US);
R. Garrett Mauldin, Erie, CO (US)

(73) Assignee: Inbone Technologies, Inc., Boulder, CO (US)

( * ) Notice: Subject to any disclaimer, the term of this patent is extended or adjusted under 35 U.S.C. 154(b) by 476 days.

(21) Appl. No.: 12/410,978

(22) Filed: Mar. 25, 2009

(65) Prior Publication Data

US 2009/0182433 A1 Jul. 16, 2009

Related U.S. Application Data

(63) Continuation of application No. 11/374,760, filed on Mar. 14, 2006, now Pat. No. 7,534,246.

(60) Provisional application No. 60/661,584, filed on Mar. 14, 2005.

(51) Int. Cl.
*A61F 2/42* (2006.01)

(52) U.S. Cl.
USPC ..................................... 623/21.18; 623/23.44

(58) Field of Classification Search
USPC ................................. 623/20.34, 21.18, 23.15
See application file for complete search history.

(56) References Cited

U.S. PATENT DOCUMENTS

| | | | |
|---|---|---|---|
| 1,090,881 | A | 3/1914 | Rowley |
| 3,872,519 | A | 3/1975 | Giannestras et al. |
| 3,889,300 | A | 6/1975 | Smith |
| 3,896,502 | A | 7/1975 | Lennox |
| 3,896,503 | A | 7/1975 | Freeman et al. |
| 3,975,778 | A | 8/1976 | Newton, III |
| 3,987,500 | A | 10/1976 | Schlein |
| 4,156,944 | A | 6/1979 | Schreiber et al. |
| 4,166,292 | A | 9/1979 | Bokros et al. |

(Continued)

FOREIGN PATENT DOCUMENTS

| | | |
|---|---|---|
| FR | 2220235 A1 | 4/1974 |
| RU | 2062072 C1 | 6/1996 |

(Continued)

OTHER PUBLICATIONS

Official Action in Japanese Patent Appln. No. 2008-501935, dated Dec. 22, 2010.

(Continued)

*Primary Examiner* — Thomas J Sweet
*Assistant Examiner* — Melissa Hoban
(74) *Attorney, Agent, or Firm* — Duane Morris LLP

(57) ABSTRACT

A prosthesis suited for orthopedic implantation possesses a multi-piece stem component that supports an artificial joint surface that can articulate with another artificial joint surface in various ways. The prosthesis can be assembled in a snap fit and/or interlocking fashion that provides positive locking means without the use of screws or other fasteners. The prosthesis can accommodate fitment of a plastic joint surface made, e.g., from ultra high molecular weight polyethylene. The prosthesis is well suited for use in an ankle replacement system that can be installed using minimally invasive intramedullary guidance established with respect to the major axis of the tibia by minimally invasive access through the calcaneus, through an incision in the bottom of the foot. The prosthesis makes possible the installation of a total ankle system using minimally invasive anterior access to the ankle joint for making bony cuts and to install prosthesis components.

15 Claims, 23 Drawing Sheets

(56) References Cited

U.S. PATENT DOCUMENTS

| | | | |
|---|---|---|---|
| 4,229,839 A | 10/1980 | Schwemmer | |
| 4,232,404 A | 11/1980 | Samuelson et al. | |
| 4,553,273 A * | 11/1985 | Wu | 623/23.45 |
| 4,676,797 A | 6/1987 | Anapliotis et al. | |
| 5,041,139 A | 8/1991 | Branemark | |
| 5,326,365 A | 7/1994 | Alvine | |
| 5,397,360 A * | 3/1995 | Cohen et al. | 623/16.11 |
| 5,766,259 A * | 6/1998 | Sammarco | 623/21.18 |
| 5,824,106 A | 10/1998 | Fournol | |
| 6,102,956 A * | 8/2000 | Kranz | 623/23.15 |
| 6,136,032 A | 10/2000 | Viladot Perice et al. | |
| 6,168,631 B1 | 1/2001 | Maxwell et al. | |
| 6,488,712 B1 | 12/2002 | Tournier et al. | |
| 6,589,281 B2 | 7/2003 | Hyde | |
| 6,663,669 B1 * | 12/2003 | Reiley | 623/21.18 |
| 6,875,236 B2 | 4/2005 | Reiley | |
| 6,926,739 B1 | 8/2005 | O'Connor et al. | |
| 2002/0055744 A1 | 5/2002 | Reiley | |
| 2002/0095214 A1 | 7/2002 | Hyde, Jr. | |
| 2003/0204263 A1* | 10/2003 | Justin et al. | 623/20.15 |
| 2004/0172138 A1* | 9/2004 | May et al. | 623/20.36 |
| 2005/0049711 A1 | 3/2005 | Ball | |

FOREIGN PATENT DOCUMENTS

| | | |
|---|---|---|
| RU | 2145822 C1 | 2/2000 |
| RU | 2149604 C1 | 5/2000 |
| RU | 2155561 C2 | 9/2000 |
| SU | 546349 | 4/1977 |
| SU | 1271509 A1 | 11/1986 |
| SU | 1533685 A1 | 1/1990 |
| WO | WO 91/07931 A1 | 6/1991 |
| WO | WO 98/07380 A1 | 2/1998 |
| WO | WO 00/15154 A1 | 3/2000 |
| WO | WO 01/19294 A1 | 3/2001 |
| WO | WO02067811 | 9/2002 |

OTHER PUBLICATIONS

Official Action in Australian Patent Appln. No. 2006223238, dated Oct. 15, 2010.

Supplementary European Search Report; EP Appln. No. 06737977, dated May 22, 2013.

* cited by examiner

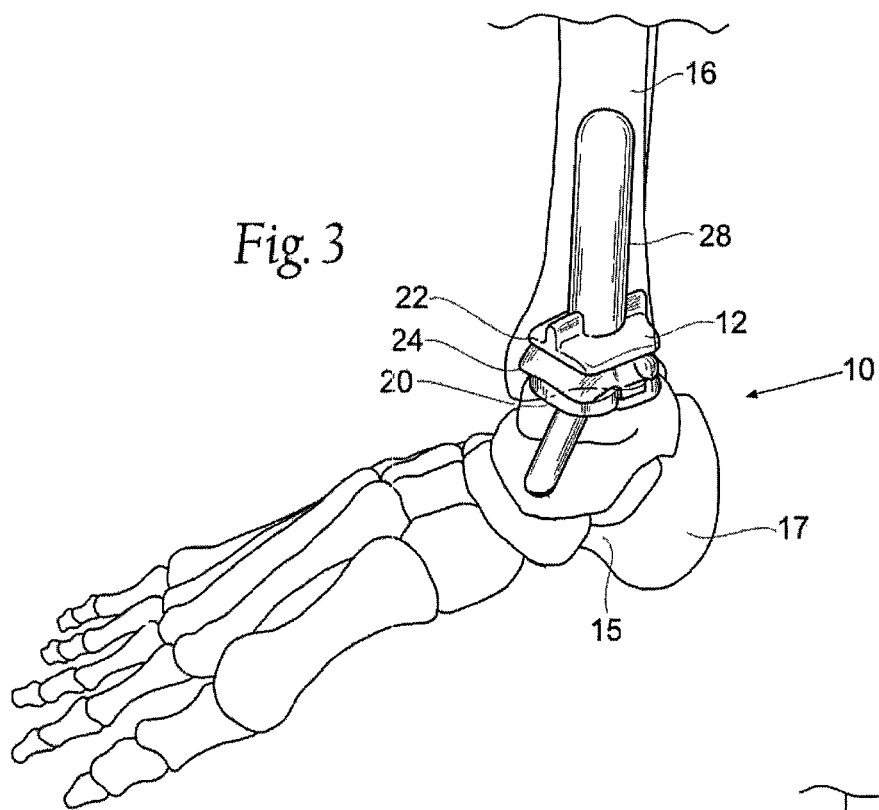
Fig. 3
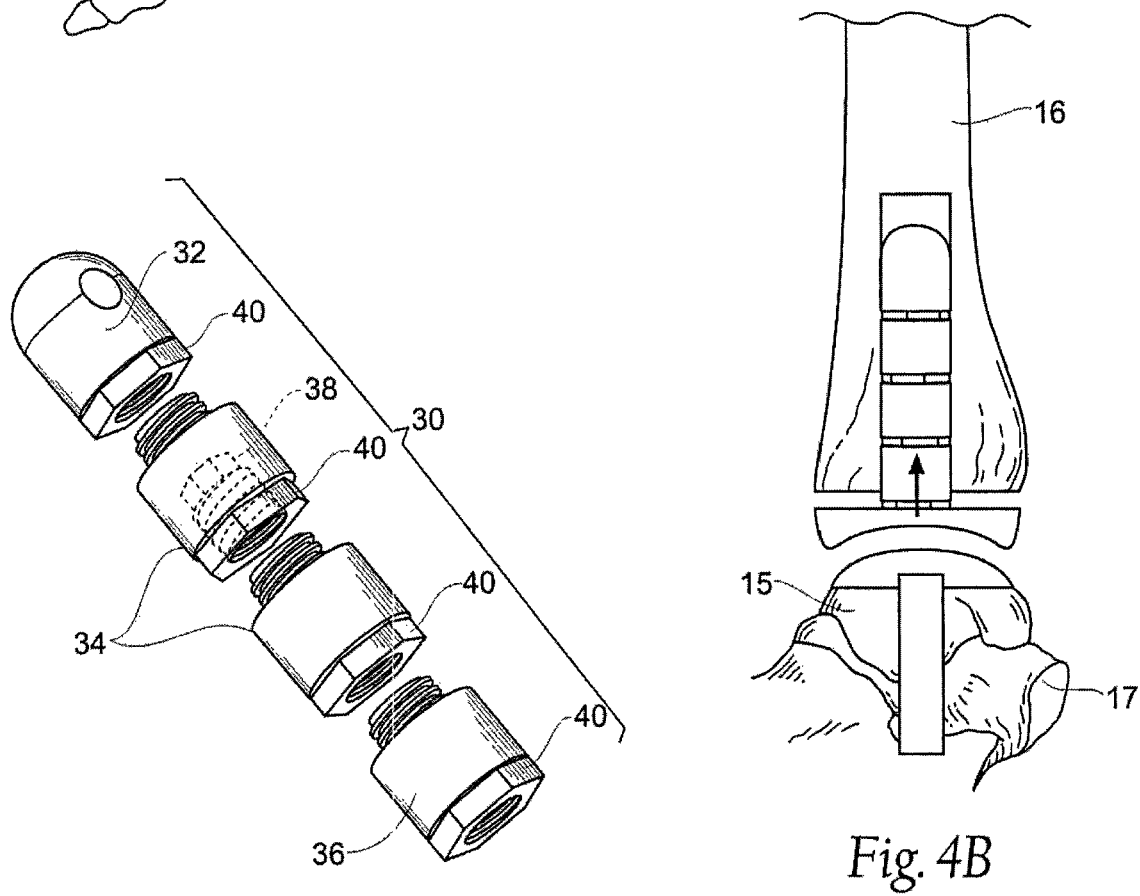
Fig. 4A
Fig. 4B

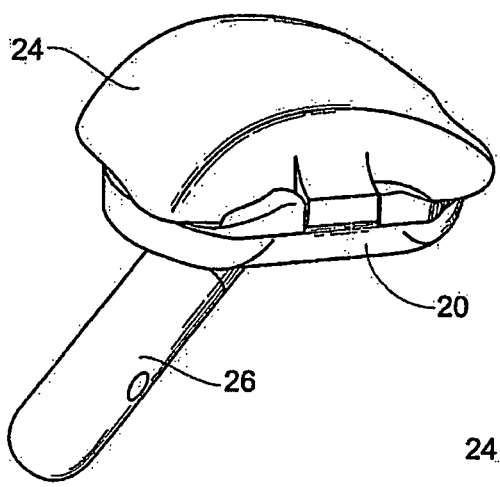
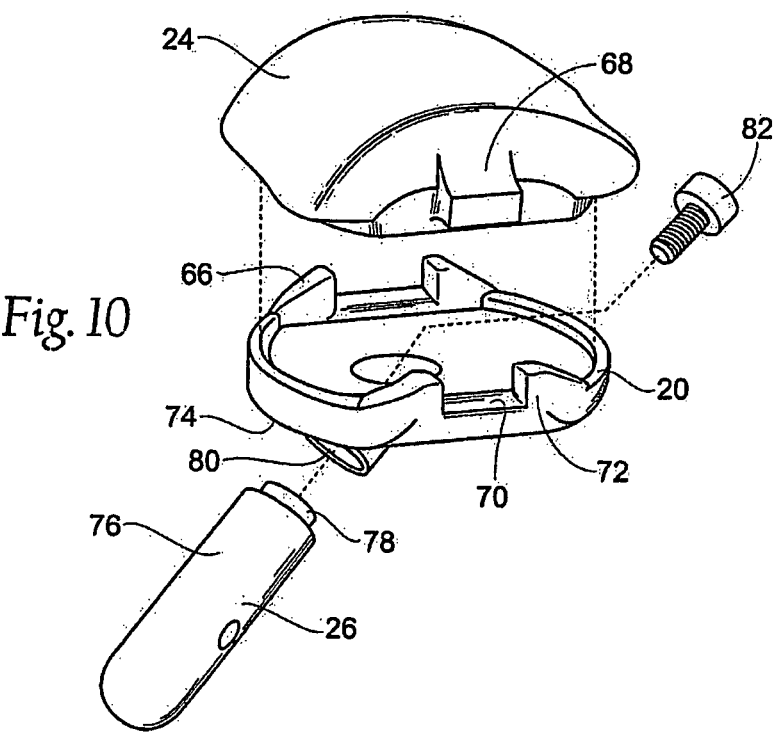
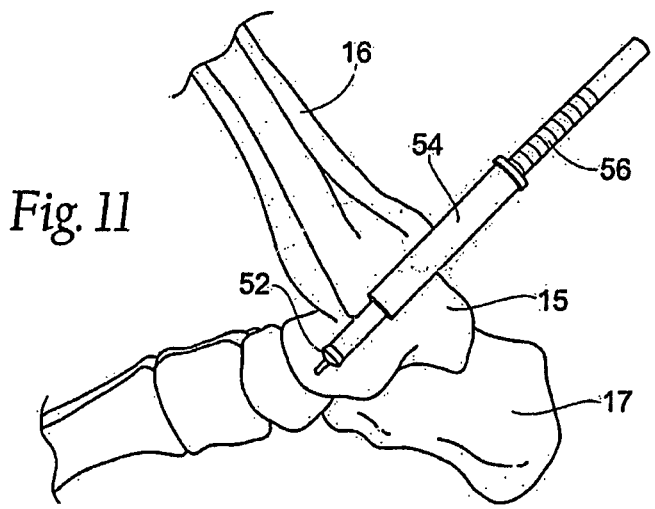

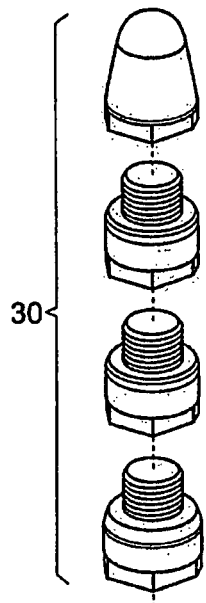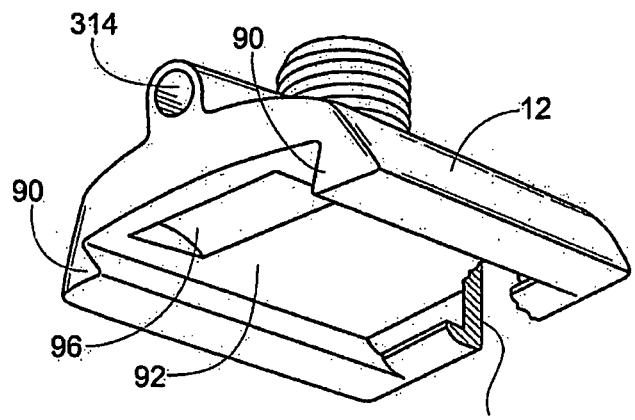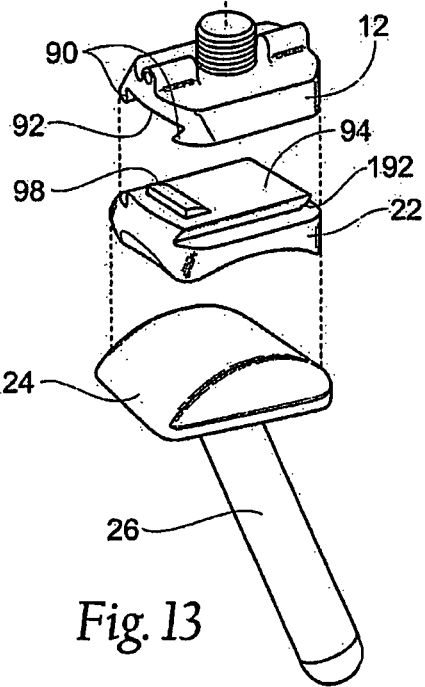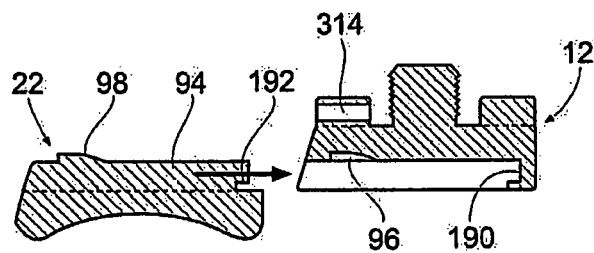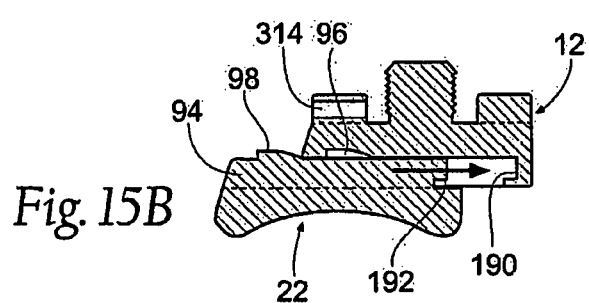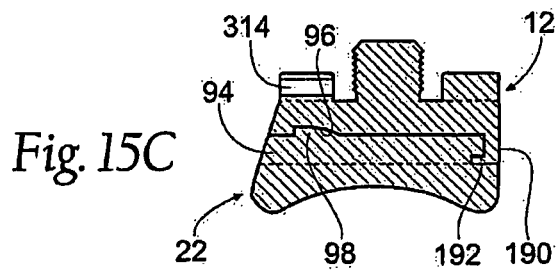
Fig. 13
Fig. 14
Fig. 15A
Fig. 15B
Fig. 15C

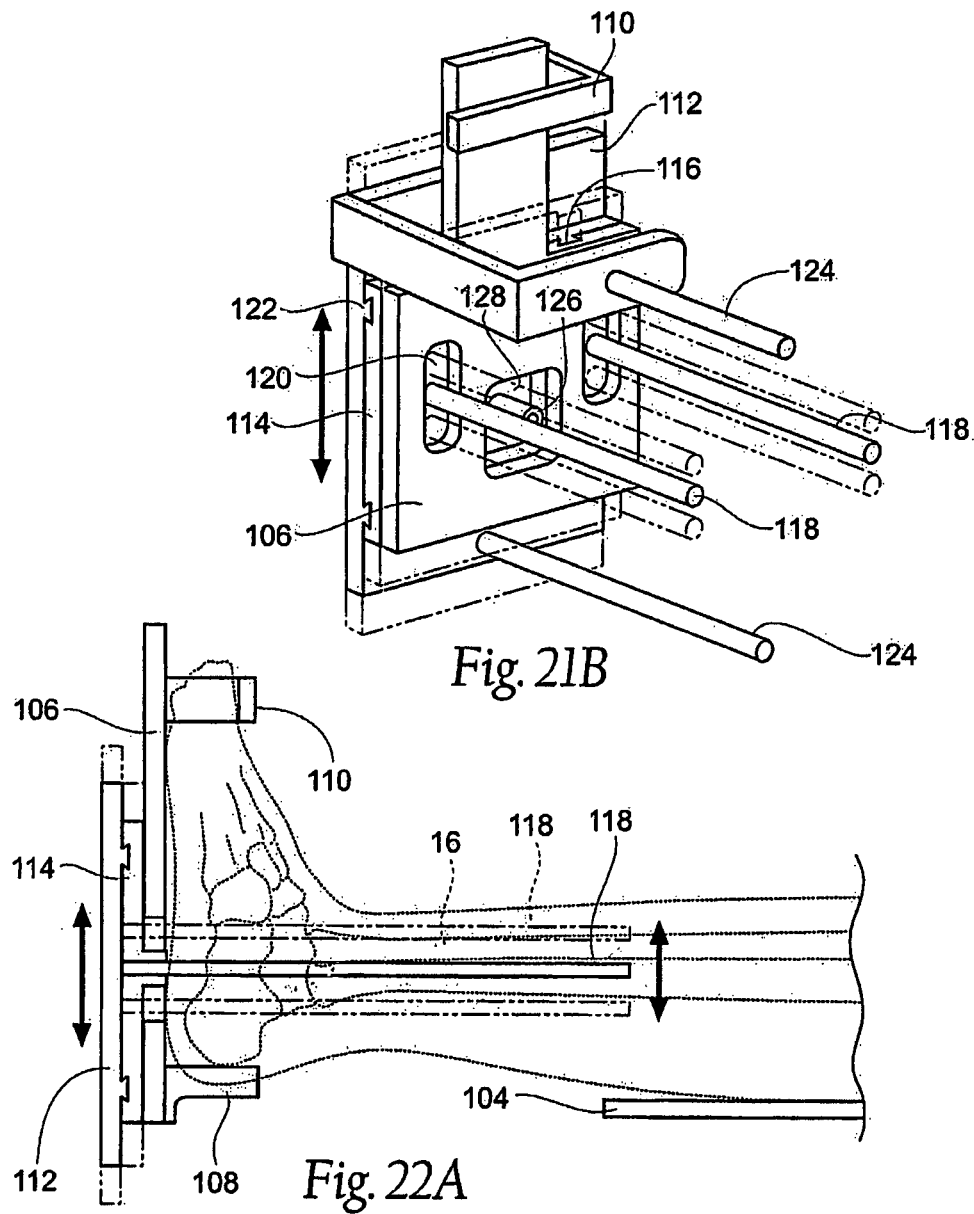
Fig. 21B
Fig. 22A
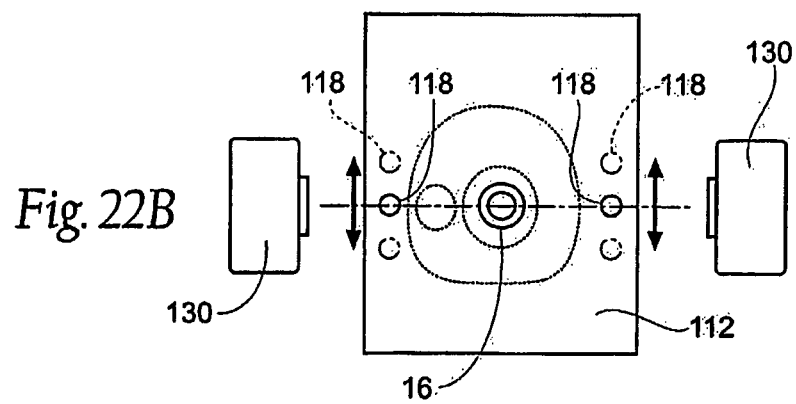
Fig. 22B

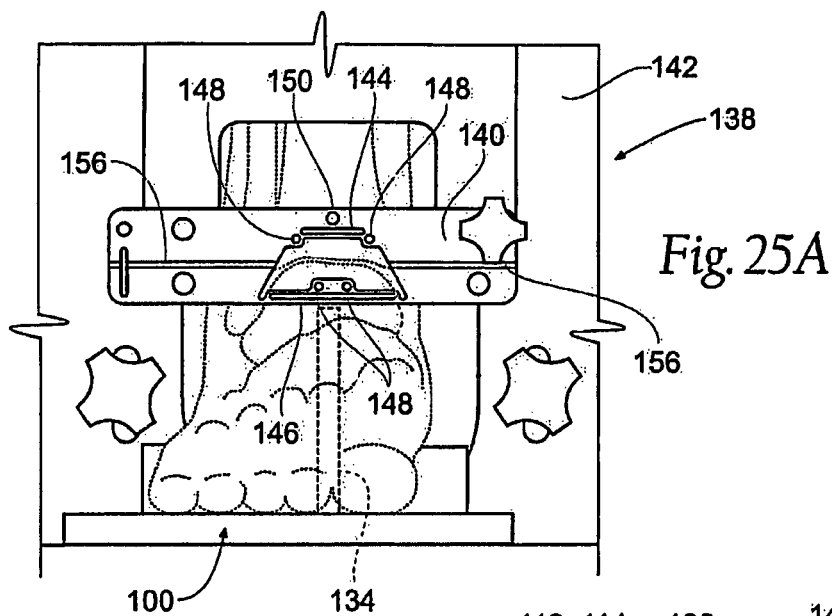
*Fig. 25A*
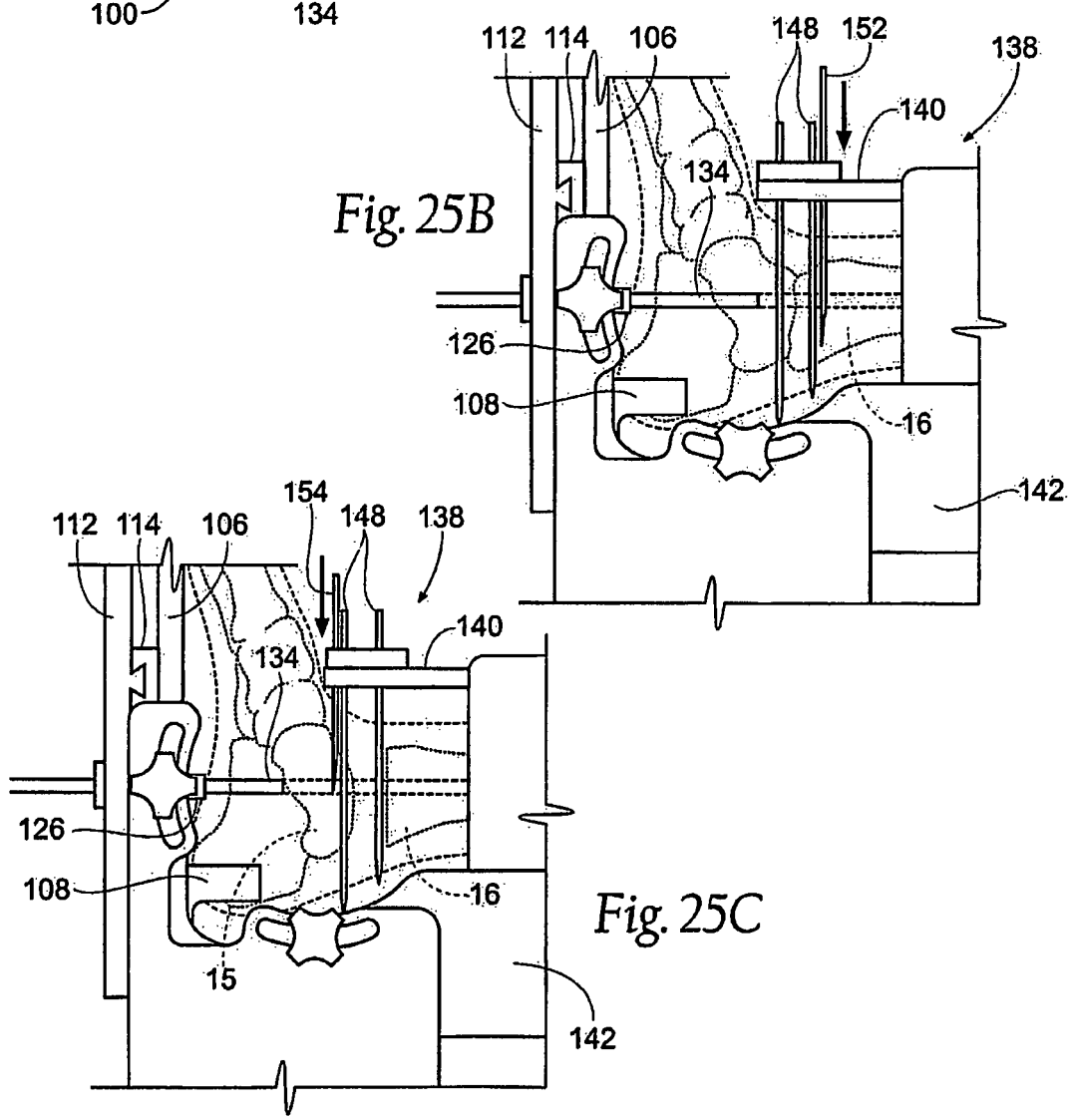
*Fig. 25B*
*Fig. 25C*

ANKLE REPLACEMENT SYSTEM

CROSS-REFERENCE TO RELATED APPLICATIONS

This application is a divisional application U.S. patent application Ser. No. 11/374,760, filed on Mar. 14, 2006, which claims the benefit under 35 U.S.C. §119(e) of U.S. Provisional Patent Application Ser. No. 60/661,584, filed Mar. 14, 2005, and is entitled "Ankle Replacement System."

FIELD OF THE INVENTION

The invention relates to ankle replacement prostheses and systems, as well as associated surgical instruments and procedures.

BACKGROUND OF THE INVENTION

Until the early to mid 1970's, patients with injured or diseased ankle joints commonly resulting from rheumatism, or degenerative or traumatic arthritis, had few options when their ankle joints failed. The most common procedure to help these patients regain some use of their ankle was obliteration of the joint by fusion, a procedure that is still commonly used today. Fusion, however, rendered the ankle stiff and generally immobile relative to the lower leg, resulting in limited use and additional stresses on the knee and hip joints.

Probably the first reported use of total ankle prosthesis was by Buckholz in 1969. The medical community recognized that such ankle replacement led to largely increased use of the ankle joint because the replacement permitted ankle ranges of motion which generally attempted to mimic the natural human joint. Since that time, ankle replacement prostheses have become increasingly common in use and improved in design.

There is, however, a need for a total ankle replacement system that reduces the occurrence of subsidence and aseptic loosening while retaining the majority of the foot's natural motion. There is also a need for a less invasive surgical method to install such a device to provide improved healing and a decreased failure rate.

SUMMARY OF THE INVENTION

The invention provides orthopedic prostheses and systems, as well as associated surgical instruments and procedures.

One aspect of the invention provides a multi-piece stem component for a prosthesis. The multi-piece stem component is suitable for use in any surgical procedure in which a stem is required for fixation of a prosthesis, whether it is a total joint implant, fusion (arthrodesis) implant, osteotomy fixation implant, or fracture fixation implant. The multi-piece stem component configuration is ideally suited for securing bone components together in a, minimally invasive procedure, in which a small surgical opening is used to install large components. Two or more small stem components can be sequentially attached to one another in situ to make a larger stem assembly. Representative tools and methodologies for installing a multi-piece stem component are also provided.

Another aspect of the invention provides articulating artificial joint surfaces comprising complementary ball-and-socket surfaces that not only articulate, but also allow the artificial joint to rotate about an axis. This makes possible more uniform wear of the surfaces to maximize function and longevity of the prostheses.

Another aspect of the invention provides articulating artificial joint surfaces comprising complementary ball-and-socket surfaces that not only articulate and rotate about an axis, but also accommodate fore and aft and lateral translation of the mating joint surfaces relative to the native bone.

Another aspect of the invention provides artificial articulating joint surfaces, each of which comprises a saddle-shaped component. The saddle shape is geometrically characterized as a swept arc, comprising a surface defined by a first arc that is swept along a second arc that is perpendicular to the first arc. The geometry forms, for each surface, an elongated trough that curves along an axis.

Another aspect of the invention provides a prosthesis supporting an artificial joint surface that can be assembled in a snap fit and/or interlocking fashion that provides positive locking means without the use of screws or other fasteners.

Another aspect of the invention provides a prosthesis accommodating fitment of a plastic joint surface made, e.g., from ultra high molecular weight polyethylene.

Another aspect of the invention provides an ankle replacement system that can be installed using minimally invasive intramedullary guidance established with respect to the major axis of the tibia by minimally invasive access through the calcaneus, through an incision in the bottom of the foot. Intramedullary guidance along the axis of the tibia makes it possible to make properly oriented bony cuts of the talus and tibia through anterior access to the ankle joint. Proper overall alignment of the total ankle system is achieved in desired alignment and orientation with all the natural axes of the native ankle joint it replaces, and improved long term results are achieved.

Another aspect of the invention provides prostheses, tools, and methodologies that make possible the installation of a total ankle system using minimally invasive intramedullary guidance established with respect to the major axis of the tibia. Desirably, minimally invasive intramedullary guidance is established with respect to the major axis of the tibia using fluoroscopic visualization.

Another aspect of the invention provides prostheses, tools, and methodologies that make possible the installation of a total ankle system using minimally invasive anterior access to the ankle joint for malting bony cuts and to install prosthesis components.

Another aspect of the invention provides prostheses, tools, and methodologies that make possible the establishment of an in-line intramedullary path through the calcaneus, talus, and tibia.

Other objects, advantages, and embodiments of the invention are set forth in part in the description which follows, and in part, will be obvious from this description, or may be learned from the practice of the invention.

DESCRIPTION OF THE DRAWINGS

FIG. 3 is a perspective anatomic view of a total ankle replacement system in which a tibial, artificial joint surface and a talar artificial joint surface are mutually sized and configured for articulation to restore a range of motion that mimics the natural joint, the system including a talar stem that supports the talar artificial joint surface and that projects from posterior to anterior of the ankle into the anterior head of the talus, without bridging the talus to the calcaneous.

FIG. 4A is a perspective exploded view of a multi-piece tibial stem that, when assembled, is sized and configured to support a tibial artificial joint surface of a type shown in either FIG. 2 or FIG. 3.

FIG. 4B is an assembled side view of the multi-piece tibial stem shown in FIG. 4A being installed in a tibia and supporting a tibial artificial joint surface in association with a talar artificial joint surface.

FIG. 9 is a perspective view of the saddle-shaped talar artificial joint surface secured in a snap-fit fashion to a talar stem having a configuration shown in FIG. 3.

FIG. 10 is an exploded perspective view of the saddle-shaped talar artificial joint surface and talar stem shown assembled in FIG. 9.

FIG. 11 is an anatomic View that illustrates a representative technique for drilling the anterior head of the talus from a posterior joint entry to install a talar stem of the type shown in FIG. 3 and FIG. 9.

FIG. 13 is a perspective exploded view of a tibial component having a tibial artificial joint surface that can comprise a plastic material, e.g., ultra high molecular weight polyethylene, and that can be assembled in a sliding snap fit fashion on a tibial stem, which is shown to be a multi-piece stem of a type shown in FIG. 4A.

FIG. 14 is a perspective view of the underside of a platform that forms a part of the tibial component shown in FIG. 13, the platform accommodating a sliding snap fit with the plastic tibial artificial joint surface.

FIGS. 15A, 15B, and 15C are side sections views of the platform shown in FIG. 14 making a sliding snap fit with the plastic tibial artificial joint surface.

FIGS. 21A and 21B are assembled perspective views of the footholder assembly shown in FIG. 20, showing its ranges of horizontal and vertical movement that make possible horizontal and vertical alignment of the leg and ankle joint radiologically.

FIGS. 22A and 22B are, respectively, side and end views of the footholder assembly shown in FIGS. 21A and 21B, showing the range of vertical movement that makes possible vertical alignment of the leg and ankle joint radiologically.

FIG. 25A is a top view of representative tools and methodologies, which serve the purpose of establishing anterior access to the ankle joint for the purpose of malting bony cuts in the talus and tibia to clear a joint space for installation of the tibial and talar prosethesis platforms.

FIGS. 25B and 25C are side views of the representative tools and methodologies shown in FIG. 25A in use to make bony cuts in the talus and tibia to clear a joint space for installation of the tibial and talar prosethesis platforms.

DESCRIPTION OF PREFERRED EMBODIMENTS

This description is divided into logical sections for ease of disclosure. Section I introduces the reader to the anatomy of the lower leg and ankle, to set the anatomic backdrop of the total ankle replacement systems and methods that will be described. Section II provides structural descriptions of representative embodiments of the tibial and talar-calcaneal components of total ankle replacement systems and devices that have the desired form, fit, and function. Section III provides descriptions of representative embodiments of systems, methods, and techniques useful for the implantation of total ankle replacement systems and devices to achieve their desired form, fit, and function.

Although the disclosure hereof is detailed and exact to enable those skilled in the art to practice the invention, the physical embodiments herein disclosed merely exemplify the invention, which may be embodied in other specific structure. While the preferred embodiment has been described, the details may be changed without departing from the invention, which is defined by the claims.

I. Anatomy of the Lower Leg and Ankle

Figure 1:
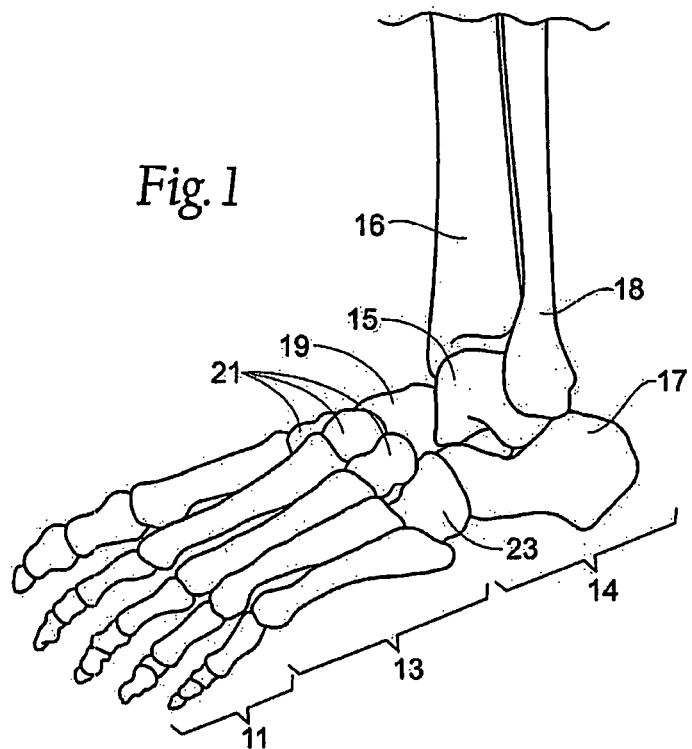
FIG. 1 is an anatomic view of a human lower leg and foot skeleton.

As FIG. 1 shows, the foot comprises fourteen phalanges or toe bones 11 connected to the metatarsus bones 13. There are also seven tarsal bones 14, of which the talus 15 supports the tibia 16 and the fibula 18, and the heel bone or calcaneus 17. Of the tarsal bones, the talus 15 and the calcaneus 17 are the largest and are adjacent to each other. The other tarsal bones include the navicular 19, three cuneiforms 21, and the cuboid 23.

II. Total Ankle Replacement System

A. Overview

Figure 2:
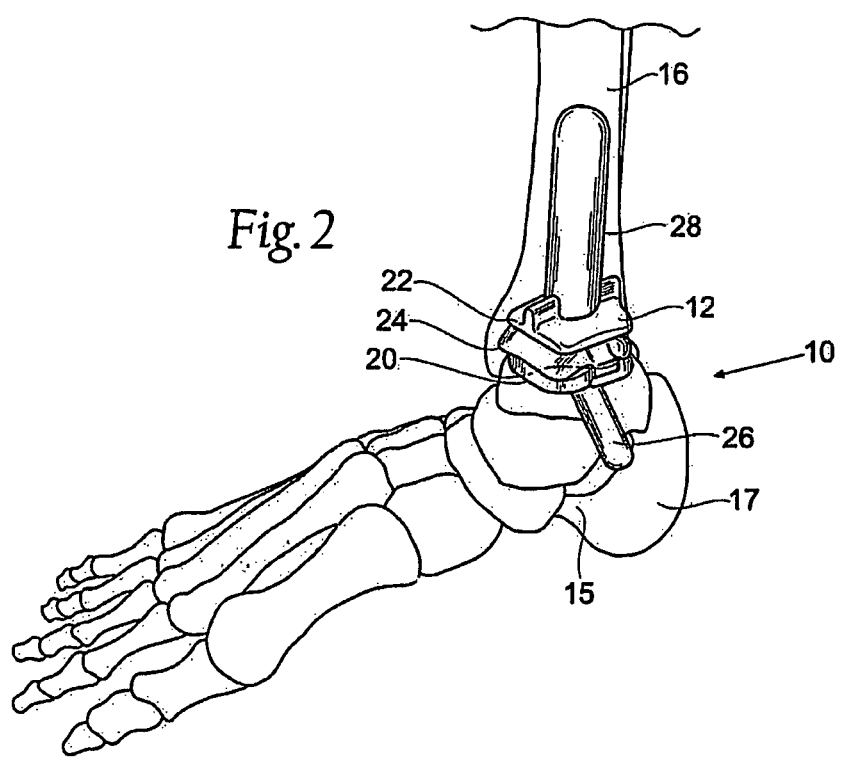
FIG. 2 is a perspective anatomic view of a total ankle replacement system in which a tibial artificial joint surface and a talar artificial joint surface are mutually sized and configured for articulation to restore a range of motion that mimics the natural joint, the system including a talar stem that supports the talar artificial joint surface and that bridges the talus to the calcaneous.

FIG. 2 shows a total ankle replacement system 10. Generally speaking, the system 10 includes a tibial platform 12 that is sized and configured for installation on the tibia 16. As also shown in FIG. 2, the tibial platform 12 desirably includes a tibial stem 28. The system also includes a talar platform 20 that is sized and configured for installation on the talus 15. As also shown in FIG. 2, the talar platform 20 includes a talar stem 26.

The tibial platform 12 carries a tibial artificial joint surface 22. The talar platform 20 carries a talar artificial joint surface 24. The tibial artificial joint surface 22 and the talar artificial joint surface 24 are bearing surfaces mutually sized and configured to articulate. The articulating joint surfaces 22 and 24 replace the natural ankle joint surfaces, which are removed (as will be described later), to restore a range of motion that mimics the natural joint.

The joint surfaces 22 and 24 may be made of various materials commonly used in the prosthetic arts including, but not limited to, polyethylene, high molecular weight polyethylene (HMWPE), rubber, titanium, titanium alloys, chrome cobalt, surgical steel, or any other total joint replacement metal and/or ceramic, bony in-growth surface, sintered glass, artificial bone, any uncemented metal or ceramic surface, or a combination thereof. The joint surfaces 22 and 24 may comprise different materials. For example, the tibial joint surface 22 may comprise a plastic or other non-metallic material, and the talar joint surface comprise a metallic material. The reverse can be true, or the surfaces 22 and 24 may each comprise the same type of materials (i.e., metal-metal or plastic-plastic).

B. Representative Embodiments

The tibial platform 12, the talar platform 20, and/or the articulating artificial joint surfaces 22 and 24 they carry may be variously configured and posses various technical features. Representative examples of configurations and features will now be described.

1. The Stems a. The Talar Stems

The talar stem 26 may be variously sized and configured. As shown in FIG. 2, the stem 26 bridges the talus to the calcaneous. This stem 26 serves the dual function of supporting the talar platform as well as fusing the sub-talar joint, should that be necessary or beneficial to the patient.

As shown in FIG. 2, the replacement system 10 incorporates many technical features disclosed in Reiley U.S. Pat. No. 6,663,669. For example, the talar platform 20 is fixed to the calcaneus 17 and/or the talus 15, which can increase the amount of bone available for fixation. The fusion of the sub-talar joint that the stem 26 provides allows fixation of the talar platform 20 to both the talus 15 and calcaneus 17. Alternatively, the subtalar joint can be fused using any method common to those of skill in the surgical arts including, but not limited to, fusion with poly(methylmethacrylate) bone cement, hydroxyapatite, a ground bone and marrow composition, plates and screws, or a combination thereof.

The enlarged available bone base provides prosthesis stability, and allows for anchoring of the talar platform 20 with, for example, screws. This design provides stability and stress absorption for the overall prosthetic ankle joint, and decreases the probability of prosthesis loosening and subsidence.

Still, prosthesis systems with talar stems 26 that do not bridge the talus to calcaneous can also offer stability, reliable fixation, and longevity. The talar stem 26 shown in FIG. 3 does not bridge the talus to the calcaneous. Instead, the stem 26 projects from posterior to anterior of the ankle into the anterior head of the talus. The talar head is a large bony component of the talus, which offers a substantial bony structure to affix the talar platform 20. The subtalar joint can be still be fused separately, if desired, using any methods just mentioned.

Any given talar stem 26 may be made of various materials commonly used in the prosthetic arts including, but not limited to, titanium, titanium alloys, tantalum, chrome cobalt, surgical steel, polyethylene, absorbable polymer, or any other total joint replacement metal and/or ceramic, bony in-growth surface, sintered glass, artificial bone, any uncemented metal or ceramic surface, or a combination thereof. The talar stem 26 may further be covered with various coatings such as antimicrobial, antithrombotic, and osteoinductive agents, or a combination thereof. These agents may further be carried in a biodegradable carrier material with which the pores of the surface of the talar stem 26 may be impregnated. See U.S. Pat. No. 5,947,893, which is incorporated herein by reference. If desired, the talar stem 26 may be coated and/or formed from a material allowing bony ingrowth, such as a porous mesh, hydroxyapetite, or other porous surface.

The talar stem 26 may be any size or shape deemed appropriate and is desirably selected by the physician taking into account the morphology and geometry of the site to be treated. The physician is desirably able to select the desired size and/or shape based upon prior analysis of the morphology of the target bone(s) using, for example, plain film x-ray, fluoroscopic x-ray, or MRI or CT scanning. The size and/or shape is selected to optimize support and/or bonding of the stem 26 to the surrounding bone(s). The stem 26 may be variable lengths from 2 cm to 12 cm and variable widths from 4 to 14 mm. In a representative embodiment, a talo-calcaneal stem 26 is approximately 65 to 75 mm in length and approximately 7 to 13 mm wide. While in the disclosed embodiment the stem has a circular cross-section, it should be understood that the stem could formed in various other cross-sectional geometries, including, but not limited to, elliptical, polygonal, irregular, or some combination thereof. In addition, the stem could be arched to reduce and/or prevent rotation, and could be of constant or varying cross-sectional widths.

The talar stem 26 may be with poly(methylmethacrylate) bone cement, hydroxyapatite, a ground bone composition, screws, or a combination thereof, or any other fixation materials common to one of skill in the art of prosthetic surgery.

As will be described in greater detail later, the talar stem 26 may additionally have interlocking components, along its length or at its top surface to assemble the stem 26 in situ and/or allow other components of the talar platform 20 to lock and/or fit into the talar stem 26.

2. The Tibial Stem

Like the talar stem 26, the tibial stem 28 may be made of any total joint material or materials commonly used in the prosthetic arts, including, but not limited to, metals, ceramics, titanium, titanium-alloys, tantalum, chrome cobalt, surgical steel, polyethylene, absorbable polymer, or any other total joint replacement metal and/or ceramic, bony in-growth surface, sintered glass, artificial bone, any uncemented metal or ceramic surface, or a combination thereof. The tibial stem 28 may further be covered with one or more coatings such as antimicrobial, antithrombotic, and osteoinductive agents, or a combination thereof. These agents may further be carried in a biodegradable carrier material with which the pores of tibial stem 28 may be impregnated. See U.S. Pat. No. 5,947,893.

Also like the talar stem 26, the tibial stem 28 may be fixed into the tibia with poly(methylacrylate) bone cement, hydroxyapatite, a ground bone composition, screws, or a combination thereof, or any other fixation materials common to one of skill in the art of prosthetic surgery. In the illustrated embodiment, the tibial stem 28 is fixed to the tibia 16 with screws. If screws are used, they can extend anteriorly, posteriorly, medially, laterally and/or at oblique angles, or any combination thereof.

The tibial stem 28 may be variable lengths from 20 mm to 300 mm and variable widths from 6 mm to 20 mm. In the preferred embodiment, the tibial stem 28 is preferably at least 50 mm in length. Of course, it should be understood that the disclosed tibial stem 28 could be of virtually any length, depending upon the size of the patient, his or her bone dimensions, and the anticipated future mobility of the patient. In general, a larger patient, having larger bones, with a high anticipated mobility (i.e. he or she will be walking/running around quite a bit) would desirably have a longer stem 28 to provide increased stability and broader distribution of stress to prevent subsidence, loosening, and tibial osteolysis. If desired, the stem 28 can incorporate an anti-rotational feature such as outwardly extending fins—for example, one or more fins, 0.5 to 25 cm long, 1 to 3 mm wide, sharp edges or dull, located along the stem 28—or a bow to the stem 28—for example, ranging from 1 to 10 degrees bow, anterior or posterior or lateral, or some combination thereof. Moreover, if desired, the surface of the tibial stem 28 can incorporate irregularities such as wedges or points, desirably angled towards the knee, which inhibit and/or prevent the tibial stem 28 from subsiding. Alternatively, the width of the tibial stem 28 may vary along the length of the stem 28, further inhibiting and/or preventing rotation and/or subsidence.

As will be described in greater detail later, the tibial stem 28 may additionally have interlocking components along its length and/or at its lower surface to allow assembly the stem 28 in situ and/or allow other components of the tibial platform 12 to lock into the tibial stem 28.

3. Multiple Piece Stem

FIG. 4A illustrates a multi-piece tibial stem 30 suitable for use in any surgical procedure in which a stem is required for fixation of an implant, whether it is a total joint implant, fusion (arthrodesis) implant, osteotomy fixation implant, or fracture fixation implant. In the illustrated embodiment, the stem 30 comprises a top (i.e., superior) component 32, one or more mid components 34, and a bottom (i.e., inferior) component 36. The top component 30 is desirably convex or domed to facilitate advancement of the stem 30 in the direction of the top component 32 within bone.

The multi-piece configuration is ideally suited for securing bone components together in a minimally invasive procedure. This configuration is also ideally suited for minimally invasive surgeries in which a small surgical opening is used to install large components. This configuration allows a small surgical opening to be used to install large components at generally a right angle to or transverse the direction of insertion of the individual stem components 32/34/36. This aspect of the multi-piece stem 30 will be very apparent after discussion of representative surgical procedure later.

Two or more small stem components 32/34/36 can be sequentially attached to one another in situ (see FIG. 4B) to make a larger stem assembly. For example, a top component 32 may be joined with a bottom component 36. Alternatively, one or more mid components 34 may be placed between the top and bottom components 32 and 36 to form a stem 30 of a desired length. The components 32/34/36 may be screwed together, as shown, or attached with a Morse taper, one-quarter turn, or other fixation means. Alternatively, the stem segments 32/34/36 can be fitted together with a combination of Morse tapers and threads, or with a combination of Morse tapers and external pins or screws.

As will be described in greater detail later, one or more of the components 32/34/36 may include an internal hex 38 or other non-rotation configuration for engagement with a driver or other tool to facilitate advancement of the component 32/34/36 within bone and/or to torque the component 32/24/36 into the adjacent component 32/34/36, as shown in FIG. 4A. Similarly, one or more of the components 32/34/36 may also include an external hex 40 or other non-rotation configuration for engagement with a wrench or other tool to grasp or otherwise secure the component 32/34/36 during installation.

As will be described in greater detail later, each component 32/34/36 is desirably sized and configured to be individually installed through a small incision, e.g., a small anterior opening in the ankle. In this way (see FIG. 4B), the individual components 32/34/36 can be sequentially joined together in situ, e.g., within an intramedullary path in the tibia (which has been reamed-out in advance) and progressively advanced up the intramedullary path, top component 32 first. The last or bottom component 36 is sized and configured to attach to a prosthesis (e.g., the tibial platform 12) that would comprise the upper half of the ankle prosthesis.

The multi-piece configuration not only permits installation using minimally-invasive procedures, but provides a means to install long fixation members or stems that might not be achievable if they were constructed of a single piece.

While the long or extended length of the multi-piece stem 30 is particularly well-suited for use in the tibia, the multi-piece stem 30 could be used in other long bones or in the talus as well.

4. The Articulating Artificial Joint Surfaces

The articulating artificial joint surfaces 22 and 24 may be made of materials such as plastic (e.g., polyethylene), ceramic, or metal, or combinations thereof (e.g., metal-backed plastic). They may possess various configurations and articulate in different ways. Various representative embodiments will now be described for purpose of illustration.

a. Mating Concave/Convex Surfaces

Figure 5:
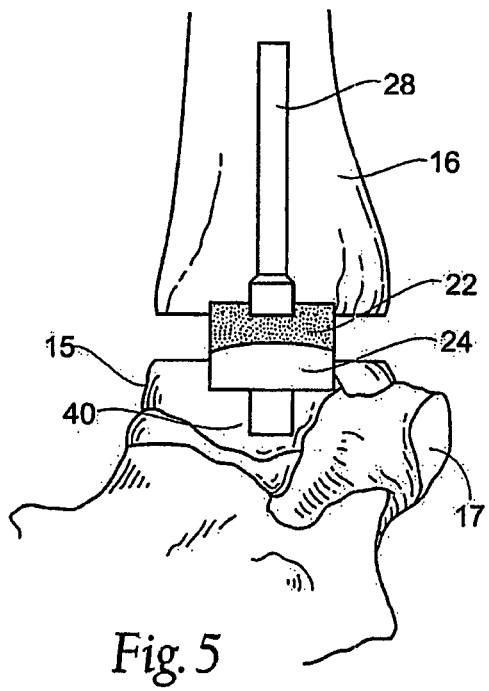
FIG. 5 is an anatomic side view of a total ankle replacement system comprising articulating ball-and-socket artificial joint surfaces.

As shown in FIG. 5, the basic geometry of the articulating surfaces 22 and 24 can form a ball-and-socket joint. In this arrangement, the articulating surfaces 22 and 24 comprise mating concave and convex surfaces. In one arrangement, the tibial artificial joint surface 22 comprises a concave dome, and the talar artificial joint surface 24 comprises a convex dome that, when installed, mates with the concave dome. This mimics the configurations of the natural joint surfaces they replace.

As FIG. 5 shows, the convex dome of the talar surface 24 can comprise a button-like structure that can be installed in a reamed-out pocket within the talus 15, without the use of a stem 26. The button-like structure can be secured within the pocket without use of a stem 26 with poly(methylmethacrylate) bone cement, hydroxyapatite, a ground bone composition, screws, or a combination thereof, or any other fixation materials common to one of skill in the art of prosthetic surgery. To facilitate placement, the button-like structure can include a peg 40 or similar appendage in lieu of a stem per se.

In this arrangement, the tibial surface 22 is secured to a stem 28 by a Morse taper connection that does not permit movement of the surface 22 relative to the stem 28.

b. Rotating Concave/Convex Surfaces

Figure 6:
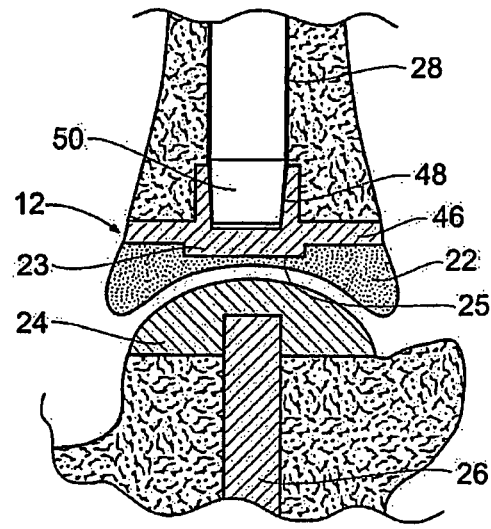
FIG. 6 is a side anatomic view of articulating artificial joint surfaces that comprise complementary ball-and-socket surfaces that not only articulate, but also allows the artificial joint to rotate about the tibial axis.

FIG. 6 illustrates an embodiment in which the articulating surfaces 22 and 24 comprise complementary ball-and-socket surfaces that not only articulate, but also allows the artificial joint to rotate about the tibial axis. This makes possible more uniform wear of the surfaces 22 and 24 to maximize function and longevity of the prostheses.

Similar to the embodiment previously described, the basic geometry of the articulating surfaces 22 and 24 comprises a ball-and-socket joint. The tibial artificial joint surface 22 comprises a concave dome, and the talar artificial joint surface 24 comprises a convex dome that, when installed, mates with the concave dome.

The talar artificial joint surface 24 is carried by a stem 26. The surface 22 is fixed to the stem 26 by a Morse-taper connection, so that no relative movement can occur between this surface 22 and the talus.

The tibial artificial joint surface 22 is carried by a platform 12. The platform 12 is, in turn, coupled to a tibial stem 28 by a Morse taper connection. No rotation between the platform 12 and the stem 28 can occur. However, the connection between the platform 12 and the joint surface 22 comprises a rotational fit. This fit is achieved between a cylindrical collar 23 depending from the platform 46 that nests within a mating trough 25 on the joint surface 22. This rotation fit allows rotation of the surface 22 relative to the platform 12 about the axis of the stem 28 and thus about the axis of the tibia, to which the stem 28 is fixed. This rotational coupling more freely accommodates rotation of the foot relative to the tibia, providing enhanced mechanical equilibrium and stability.

c. Translating Surfaces

Figure 7A:
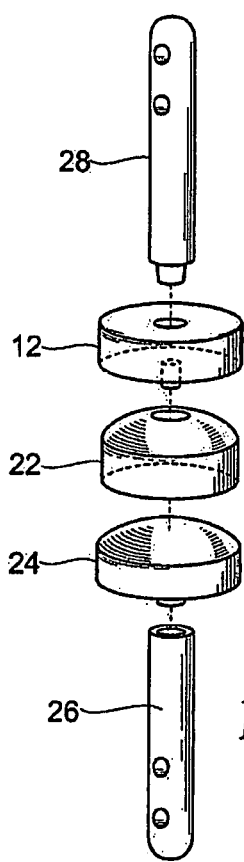
FIG. 7A is an exploded perspective view of articulating artificial joint surfaces that comprise complementary ball-and-socket surfaces that not only articulate and rotate about the tibial axis, but also accommodate fore and aft and lateral translation of the mating joint surfaces relative to the tibia.
Figure 7B:
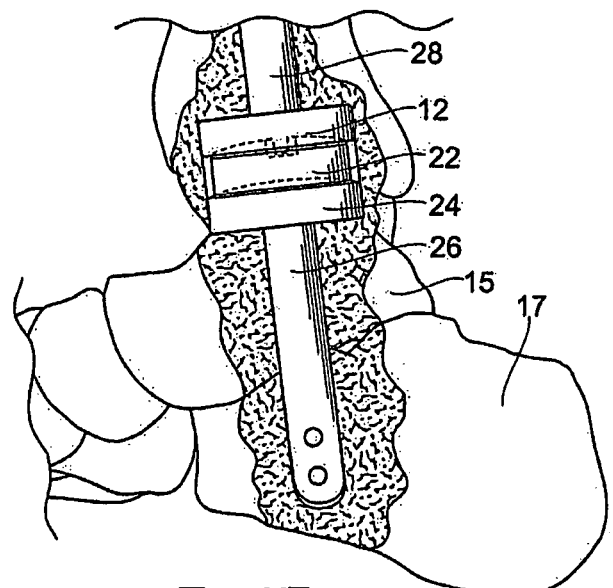
FIGS. 7B and 7C are side anatomic view of articulating artificial joint surfaces shown in FIG. 7A when assembled and installed for use.
Figure 7C:
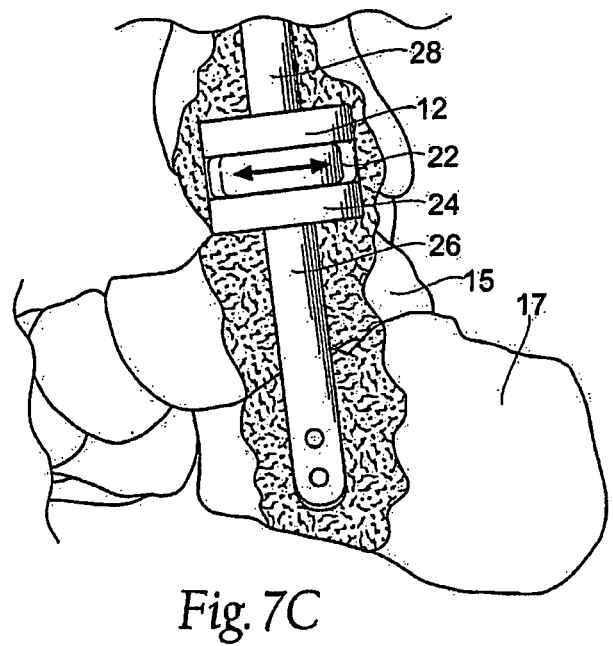

FIGS. 7A, 7B, and 7C illustrate an embodiment in which the articulating surfaces 22 and 24 comprise complementary ball-and-socket surfaces that not only articulate and rotate about the tibial axis, but also accommodate fore and aft and lateral translation of the mating joint surfaces relative to the tibia.

As in previous arrangements (see FIGS. 7A and 7B), the tibial artificial joint surface 22 comprises a cup or socket-like surface, and the talar artificial joint surface 24 comprises a ball-like surface that, when installed, mates with the cup-like surface of the tibial artificial joint surface 22.

Also as in previous arrangements (still referring to FIGS. 7A and 7B), the talar artificial joint surface 24 is carried by a stem 26. The surface 22 is fixed to the stem 26 by a Morse-taper connection, so that no relative movement can occur between this surface 22 and the talus.

The tibial artificial joint surface 22 is carried by a platform 12. The platform 12 is, in turn, coupled to a tibial stem 28 by a Morse taper connection. No rotation between the platform 12 and the stem 28 can occur. However, the connection between the platform 12 and the joint surface 22 comprises a loose, non-interference fit between an oversized hole 42 in the joint surface 22 and a lesser diameter tab 44 on the platform 12. This loose coupling permits relative lateral (side-to-side) as well as anterior-to-posterior sliding or translation between the platform 12 and the joint surface 22 (see FIG. 7C), as well as intermediate ranges of diagonal movement. The loose coupling also allows rotation of the surface 22 relative to the platform 12 about the axis of the stem 28.

This loose coupling accommodates forward and sideways translation of the foot relative to the tibia, as well as rotation of the foot relative to the tibia. This feature makes possible uniform wear and uses all the surface area to the fullest extent to maximize function and longevity of the prostheses. The translating ball and socket type articulation provides mechanical equilibrium and stability. The articulating spherical surfaces 22 and 24 maximize the contact area, thereby minimizing the contact pressure. This minimizes local surface stresses, in turn, minimizing wear on the joint and maximizing joint longevity.

The ball joint maximizes joint mobility. It accommodates the normal flexure of the ankle during walling or running. It also allows for the normal side to side rotation of the normal ankle.

d. Saddle Surfaces

Figure 8A:
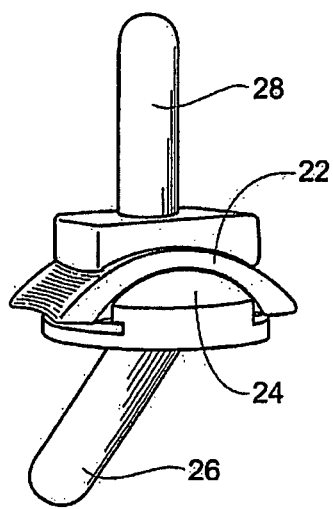
FIGS. 8A, 8B, and 8C are the articulating tibial and talar surfaces 22 and 24 are perspective views of articulating artificial joint surfaces that each comprise a saddle-shaped component, with arrows provided in FIGS. 8B and 8C showing the articulation of the surfaces during up-and-down flexing of the foot (FIG. 8B) and side-to-side flexing of the foot (FIG. 8C).

Previous embodiments show, as the basic articulating geometry, ball and socket joints. In FIG. 8A, the articulating tibial and talar surfaces 22 and 24 are shown to each comprise a saddle-shaped component. The saddle shape is geometrically characterized as a swept arc (which is of constant radius in a preferred embodiment), comprising a surface defined by a first arc (which is of constant radius in a preferred embodiment) that is swept along a second arc (which is also of constant radius in a preferred embodiment) that is perpendicular to the first arc. The geometry forms, for each surface 22 and 24, an elongated trough that curves along an axis.

As shown in FIG. 8A, the trough of the tibial saddle surface 22 component nests within the trough of the talar saddle surface 24. An interface is thereby formed between the tibial and talar components of the prosthesis. The articulation occurs along this interface both along the curved axis of the trough, i.e. accommodating up and down flexing of the foot (see FIG. 8B), as well as transversely within the tough, i.e., accommodating lateral (side to side) flexing of the foot (see FIG. 8C).

The saddle interface provides the joint with intrinsic stability, as the joint wants to assume a position of stable static equilibrium. Some patients will require a deep saddle trough because the surrounding soft tissue supports for the ankle joint are compromised or weak. Other patients may require a less deep saddle trough because their joint has more supporting soft tissue. A more shallow saddle trough provides increased ability for the joint to rotate about the tibial axis, which is desirable.

Figure 8B:
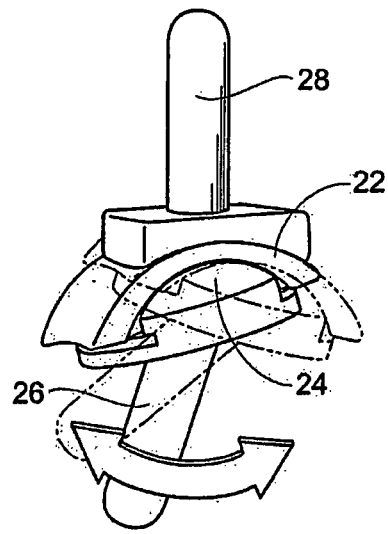
Figure 8C:
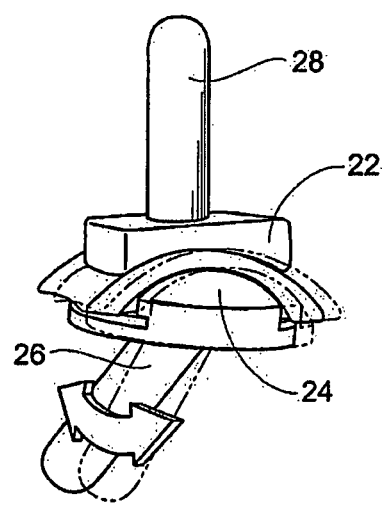

As FIGS. 8A to 8C show, the saddle shaped tibial surface 22 can be sized and configured to be fixed to a tibial stem 28 in any of the manners previously described. In FIGS. 8A to 8C, the stem 28 can comprise comprises a multi-piece stem 30 as earlier described and as shown in FIG. 4A. The talar component is desirably installed after the tibial component has been inserted into the joint.

The talar component can be sized and configured in various ways. In the embodiment shown in FIGS. 9 and 10, the talar platform 20 is secured to a talar stem 26 having a configuration shown in FIG. 3, i.e., the stem 26 does not bridge the sub-talar joint, but projects from posterior to anterior into the anterior head of the talus 15.

FIG. 11 illustrates a representative technique for drilling the anterior head of the talus 15 from a posterior joint entry to install the talar stem 26. A k-wire 52 is used to pierce from within the joint, in an anterior to posterior-lateral direction. The foot is then placed in the dorsi-flexion position, as shown. A conventional cannulated trocar (not shown) is placed over the k-wire 52 and advanced to pierce the joint in a posterior to anterior direction. A cannula 54 is passed over the trocar, and the trocar is removed. The cannula 54 remains, establishing a percutaneous path to the talus 15. A cannulated drill 56 is placed over the k-wire 52 within the cannula 54. The anterior head of the talus 15 is drilled to the proper depth to receive the stem 26. The stem 26 is inserted.

The talar platform 20 is secured to the stem 26 and nests on top of the talus 15, which has been milled beforehand. As FIG. 10 best shows, the proximal end 76 of the stem 26 includes a male hex 78, or other non-rotation configuration, that nests in a female hex 80 on the bottom 74 of the talar platform 20. A cap screw 82, proceeding through the talar platform 20 into the talar stem 26, affixes the stem 26 and platform 20 together.

In the illustrated embodiment, the saddle shaped talar artificial joint surface 24 snaps into the top of the talar platform 20 and rests in a load bearing nest defined by the platform 20. A pair of opposing tabs or protrusions 68 from both sides of the talar artificial joint surface 24 nest in slots 70 in raised pillars 72 on the talar platform 20, further ensuring that the surface 24 is well secured to the talar platform 20. The snap-together interlocking configuration provides for easily removal and replacement of the talar artificial joint surface 24.

Before installing the surface 24, a sizing-piece, made of plastic or other suitable biocompatible material, can be slid into the joint space so the physician can determine the proper thickness of material to provide the proper joint distention. When the proper size has been determined, the physician slides the actual talar artificial joint surface 24 into the joint space and snap-fits it onto the platform 20.

This arrangement makes it possible to install and use a plastic joint surface on the talar side of the prosthesis. For example, the talar artificial joint surface 24 can be formed of a durable biocompatible plastic, e.g., Ultra High Molecular Weight Polyethylene (UHMWPE). Placement of a plastic component on the talar side rather than on the tibial side provides the maximum amount of plastic material available for strength and wear properties, while at the same time allowing for the minimal amount of bone removal.

Figure 12A:
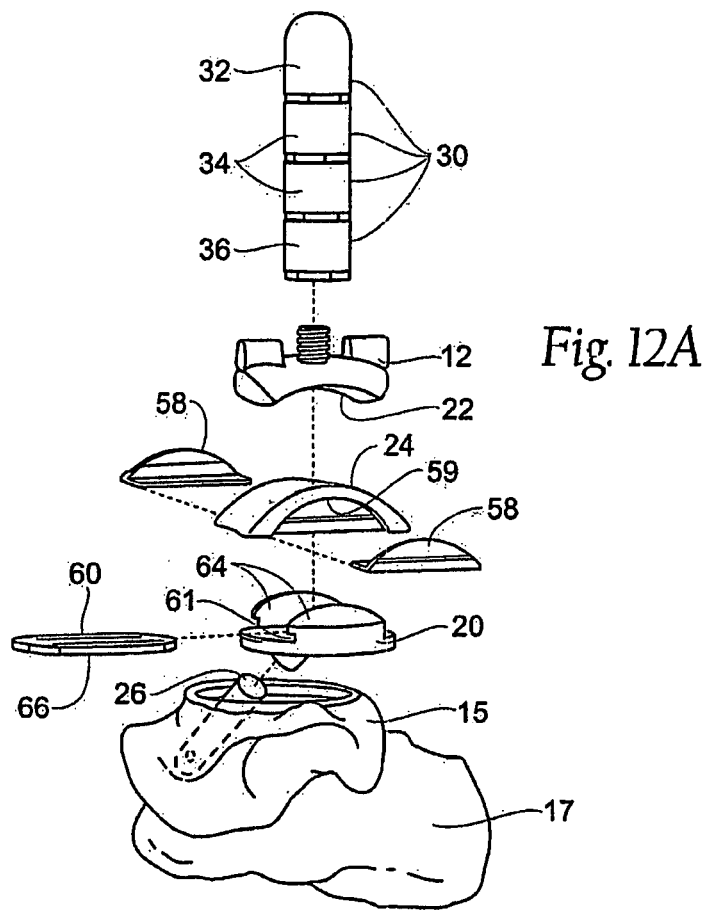
FIG. 12A is a perspective exploded view of a total ankle replacement system that includes a tibial component that articulates with a talar component having a talar artificial joint surface that can comprise a plastic material, e.g., ultra high molecular weight polyethylene, and that can be assembled in an interlocking fashion on a talar stem.
Figure 12B:
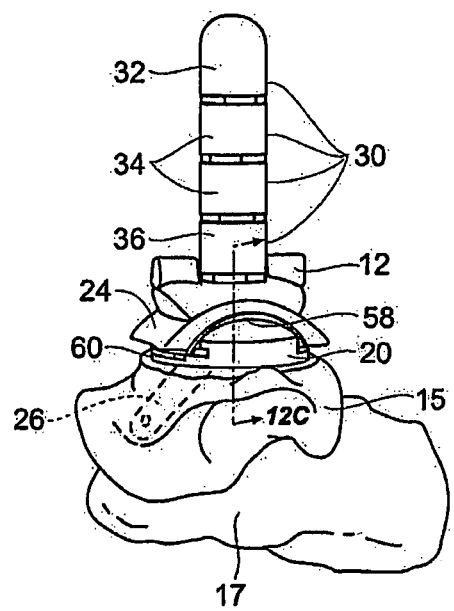
FIG. 12B is a perspective assembled view of the total ankle replacement system shown in FIG. 12A.
Figure 12C:
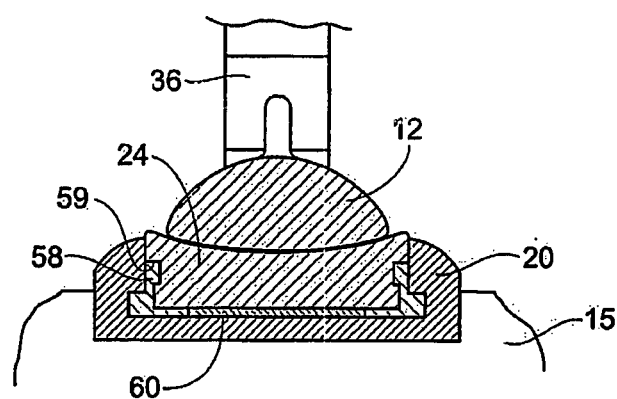
FIG. 12C is a section view taken generally along line 12C in FIG. 12B.

Another representative embodiment of a plastic talar-side component is shown in FIGS. 12A and 12B. The component shares many of the features of the component just described. In addition, the joint surface 24 rests on the platform 20 upon a pair of spacing leg plates or spacers 58. The spacers 58 are placed under the talar artificial joint surface 24 on opposing sides of the surface 24 (see FIG. 12C). The spacers 58 include upwardly arched sides that nest within tabs 59 extending beneath the arched edges of the saddle-shaped joint surface 24. A locking plate 60 fits on the platform 20 beneath the spacers 58 upon which the talar artificial joint surface 24 rests. Flanges 66 projecting from sides of the locking plate 60 lock into slots 61 on the talar platform 20.

The thickness and configuration of the spacers 58 and plate 60 can be varied to accommodate individual patient needs and anatomy. In a representative embodiment, the spacers 58 and locking plate 60 are each approximately 1-2 mm thick.

The locking plate 60 is sized and configured with a memory to serve as a spring-lock. All the components of the talar assembly are frictionally locked together, like a rubix cube, without the use of screws or other mechanical fasteners.

The frictionally interlocking design provides stability, as there are no induced forces tending to drive the components from the joint space, because they are all interlocked. The anterior-posterior and medial-lateral forces on the talar component may be substantial, but the talar joint surface 24 is trapped-locked within the talar platform 20 sidewalls and securely held in place.

The snap-together interlocking system just described provides a positive locking means without the use of screws or other means. The interlocking design also provides the physician with a relatively simple means to replace the talar artificial joint component 24 if it wears out. To replace the high-wear component 24, the physician makes a small anterior opening in the ankle to access the joint. The physician then removes the locking plate 60 and spacers 58 and withdraws the worn component 24. A new component 24 is inserted and locked into place.

5. Plastic, Snap Fit Tibial Component

A snap-fit assembly can also be incorporated into a tibial component. As shown in FIG. 13, a tibial platform 12 includes a tibial stem 30, which is shown to comprise a multi-piece stem as earlier described and as shown in FIG. 4A. In this embodiment, the tibial platform 12 and the stem 30 desirably comprise metal parts.

The tibial platform 12 carries a tibial artificial joint surface 22. The joint surface 22 is desirable made from a durable biocompatible plastic, e.g., Ultra High Molecular Weight Polyethylene (UHMWPE). Desirably, the plastic selected for the joint surface 22 is resiliently deformable, meaning that it will temporarily yield or bend in response to an applied force, but it will not permanently deform, but rather will return to its normal configuration when the force is removed. With this feature, the joint surface 22 can be sized and configured to be snap-fitted to the platform 12. It should be appreciated that alternative snap-fit assemblies could comprise a metal joint surface 22 and a resilient platform 12, or resilient platform 22 and a resilient joint surface 12.

To secure the joint surface 22 to the platform 12, as FIG. 13 shows, the platform 12 includes oppositely spaced, inwardly tapered side rails 90. The side rails 90 extend in an anterior to posterior direction along the underside of platform 12. The tapered side rails 90 form a channel 92 between them.

The topside of the artificial joint surface 22 (see FIG. 13) includes a tab member 94. The tab member 94 is sized and configured to nest within the channel 92, by sliding the tab member 94 into the channel 92 in an anterior to posterior direction, as FIGS. 15A to 15C show.

As FIG. 14 shows, the underside of the platform 12 includes a shaped depression or notch 96 near its anterior edge. Likewise, the topside of the artificial joint surface 22 includes an upwardly projecting lobe or detent 98 near its anterior edge. The detent 98 is sized and configured to rest within the notch 96.

More particularly, by applying force, the tab member 94 is made to enter and slide within the channel 92 (see FIG. 15A). The upwardly projecting detent 98 will ultimately contact the anterior edge of the platform 12. As sliding force continues to be applied, the anterior edge of the resilient artificial joint surface 22 will yield by bending (see FIG. 15B). The detent 98 will, as a result, ride under the anterior edge of the platform 12 and slide along the underbody of the platform 12, until the notch 96 is encountered (see FIG. 15C). When the notch 96 is encountered, the resilience of the joint surface 22 will snap-fit the detent 98 into the notch 96.

As FIGS. 13 and 14 show, the underside of the platform 12 desirably includes a stop flange 190 along its posterior edge. The joint surface 22 includes a mating proximal groove 192, which nests against the stop flange 190 to prevent over-travel of the joint surface 22 relative to the platform when caused to slide in a posterior direction. The engagement of the stop flange 190 and groove 92 is sized and configured to occur in concert with the snap-fit engagement of the detent 98 within the notch 96.

Figure 15D:
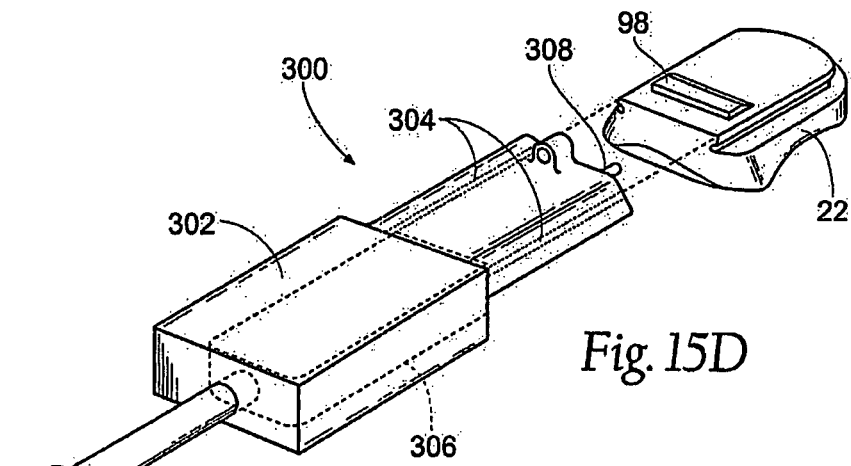
FIGS. 15D, 15E, and 15F are perspective views of an installation tool being manipulated to male the sliding fit between the plastic tibial artificial joint surface and the platform as shown in FIGS. 15A, 15B, and 15C.
Figure 15E:
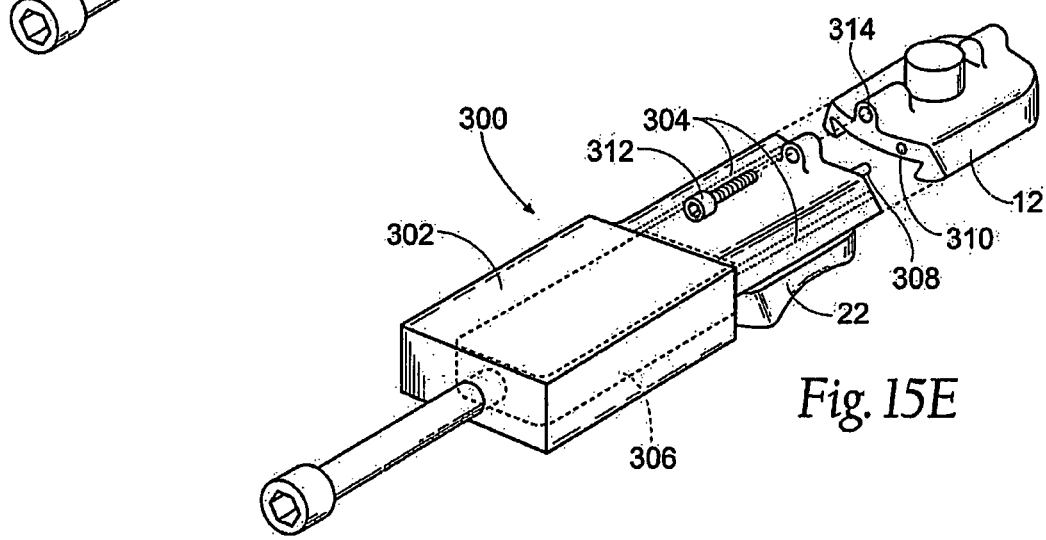
Figure 15F:
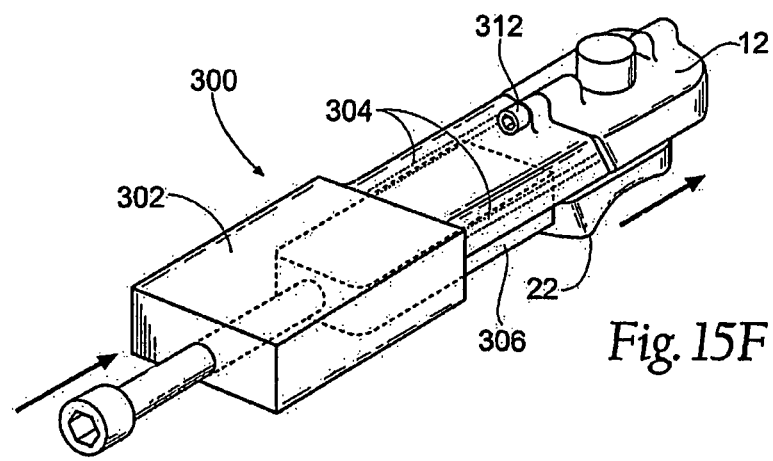

As FIGS. 15D to 15F show, an installation tool 300 can be provided to aid in sliding the joint surface 22 into fitment with the platform 12.

In the illustrated embodiment, the installation tool 300 includes a body 302 defining a channel 304 in which a manually operable plunger 306 is carried for fore and aft sliding movement. With the plunger 306 pulled back into its most-aft position (see FIG. 15D), the joint surface 22 can be loaded into the channel 304, detent 98-side first (the tab member 94 slides within side rails that line the channel 304). The joint surface 22 is placed into abutment with the plunger 306 within the channel 304.

As FIG. 15E shows, the platform 12 is coupled to the distal end of the body 302 (e.g., with a mounting screw 312 carried on the distal end of the body 302 that engages a threaded receptacle 314 on the platform 12, along with an anti-rotational holding pin 308 on body 302 that fits within an aperture 310 on the platform 12). The body 302 holds the channel 92 of the platform 12 in alignment to accept the tab member 94 of the joint surface 22.

As FIG. 15F shows, forward advancement of the plunger 306 pushes the joint surface 22, expelling it from the body channel 304 and into the platform channel 92, until the notch 96 and detent 98 engage (as FIG. 15C shows). Disengaging the screw 312 from the receptacle 314 and pulling back on the tool 300 disengages the holding pin 308 from the aperture 310, freeing the tool 300 from the now-assembled tibial component.

Figures 16, 17:
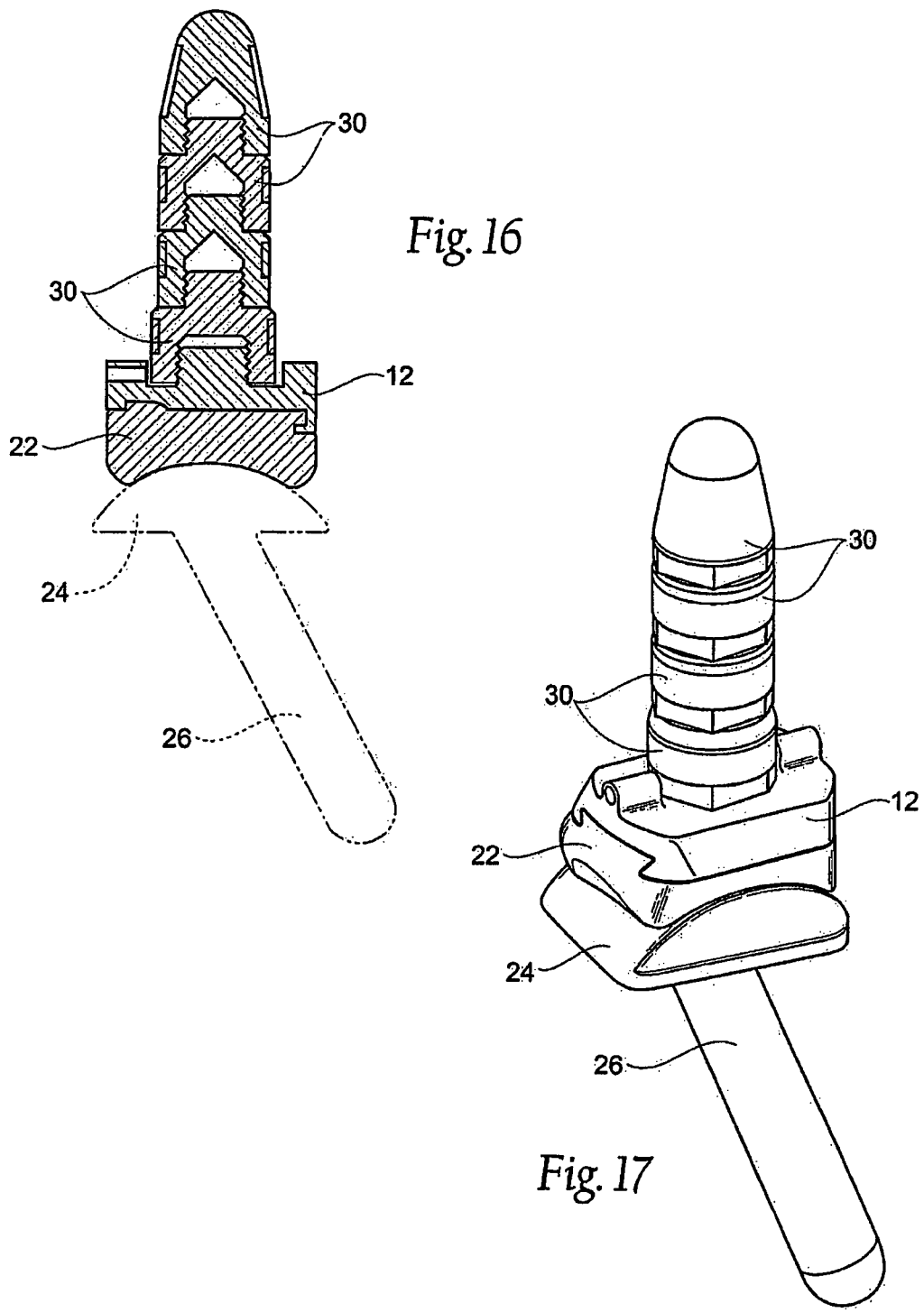
FIG. 16 is a side section view of the tibial component shown in FIG. 13, after assembly.
FIG. 17 is a perspective view of the tibial component shown in FIG. 13, after assembly, and in articulation with a talar component.

When the tibial component is assembled (see FIG. 16), the tab member 94 of the joint surface 22 is captured within the side rails 90 of the platform 12; the detent 98 if the joint surface 22 is captured within the notch 96 of the platform; and the proximal groove 192 of the joint surface 22 is captured within the stop flange 190 of the platform 12. As a result, the joint surface 22 is held securely within the platform 12, which is, in turn, fixed in position by the stem 30. The joint surface 22 is thereby positioned for stable articulation with a talar artificial joint surface 24 (see FIG. 17), which is, in turn, fixed in position by a stem 26.

III. Implantation

A. Intramedullary Guidance

Desirably, the ankle replacement system 10 is installed using minimally invasive intramedullary guidance. Intramedullary guidance is established with respect to the major axis of the tibia by minimally invasive access through the calcaneus, through an incision in the bottom of the foot. Intramedullary guidance along the axis of the tibia makes it possible to make properly oriented bony cuts of the talus 15 and tibia 16 through anterior access to the ankle joint. Proper overall alignment of the total ankle system 10 and improved long term results are achieved.

Figure 18:
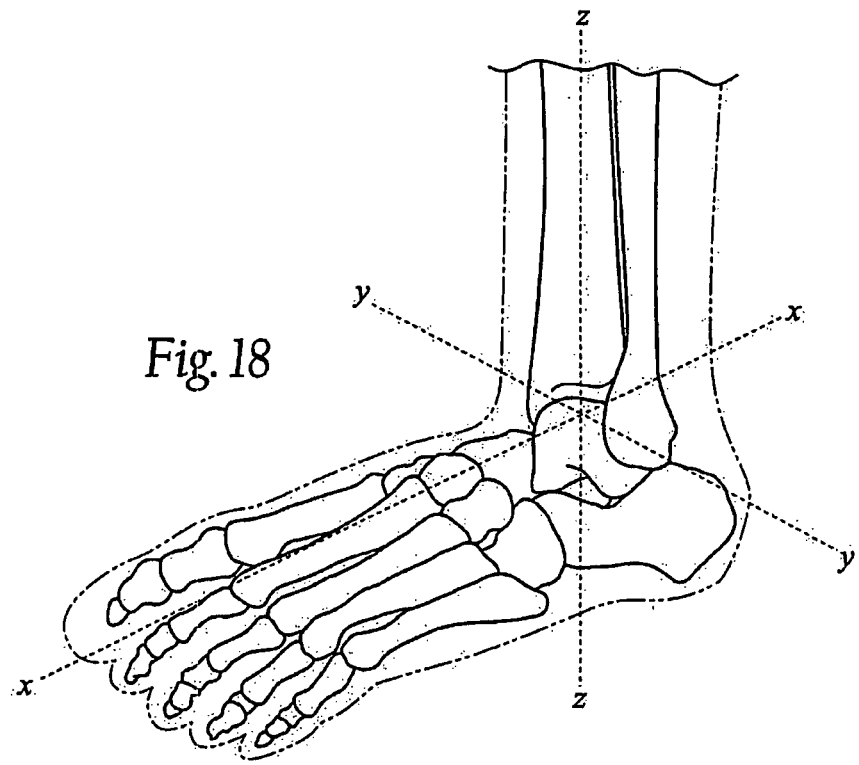
FIG. 18 is a perspective anatomic view of a native ankle joint, showing the three natural X, Y, and Z axes of the joint.

Using installation tools, systems, and methods that incorporate intramedullary guidance, the total ankle system 10 can be installed in desired alignment and orientation with all the natural axes of the native ankle joint it replaces. FIG. 18 shows these natural axes to include the anterior to posterior axis (Y-horizontal axis) of rotation of the ankle joint, the natural medial-to-lateral axis (X-horizontal axis) of rotation of the ankle joint, and the natural superior-to-inferior axis (Z-vertical axis) of alignment of the ankle joint with the major axis of the tibia. By establishing and maintaining proper alignment of the anterior to posterior axis (Y-horizontal axis) of rotation, the ankle replacement system 10 establishes and maintains the desired degree of plantar-dorsi ("up and down") flexion of the foot. By establishing and maintaining proper alignment of the natural medial-to-lateral axis (X-horizontal axis) of rotation, the system 10 establishes and maintains the desired degree of inversion/eversion ("in and out") rotation of the foot. By establishing and maintaining proper alignment of the natural superior-to-inferior axis (Z-vertical axis) of alignment of the ankle joint with the long axis of the tibia, the system 10 is accurately oriented with respect to the central tibial axis of the leg, so that intramedullary support can be achieved by in line drilling of the calcaneous 17 and talus 15 in a single drilling step using fluoroscopic guidance.

B. Installation Tools, Systems, and Methods

Representative installation tools, systems, and methods will be described that are ideally suited for use in ankle replacement procedures (i.e., the installation of a prosthetic replacement for either or both of the tibial and talar ankle joint surfaces), as well as procedures involving fusions in an ankle replacement procedure (e.g., subtalar fusions, pan-talar fusions, or triple arthrodeses).

The representative installation tools, systems, methods accomplish the tasks of (i) the alignment of the ankle joint with the tibia, (ii) the establishing of an in-line intramedullary path through the calcaneus, talus, and tibia; (iii) the establishing of anterior access for the purpose of making properly oriented bony cuts in the talus and tibia to install the tibial and talar platforms 12 and 20; (iv) the installation of the tibial and talar platforms 12 and 20.

Representative embodiments of each of these tasks and related tools, systems, and methods will now be described.

1. Alignment of the Ankle Joint with the Tibia

Figure 19:
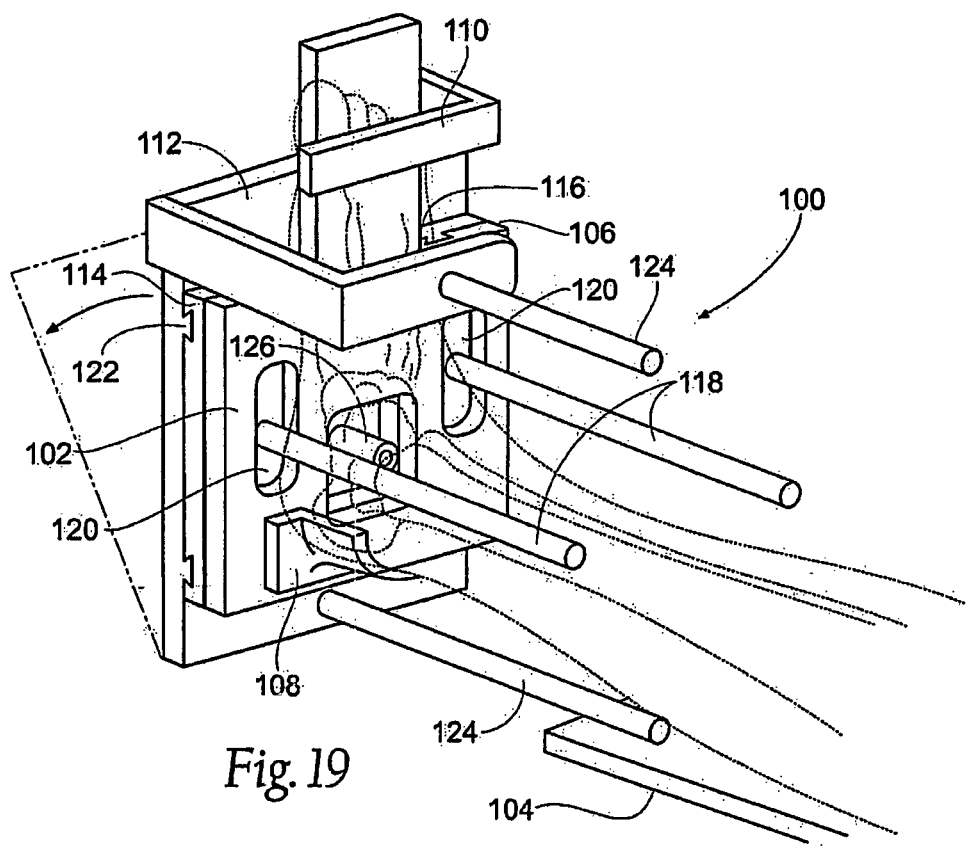
FIG. 19 is a perspective view of an alignment tool, which serves the task of aligning an ankle joint with the tibia during a procedure which installs a total ankle replacement system of a type shown in previous figures.

FIG. 19 shows a representative alignment tool 100, which serves the task of the alignment of the ankle joint with the tibia during a prosthesis installation procedure. The alignment tool 100 includes a footholder assembly 102 and a leg rest 104. The footholder assembly 102 includes a foot rest 106, to which the foot is secured by a foot clamp 106 and heel clamps 108 during an prosthesis installation procedure. The calf of the leg is suitably secured to the leg rest 104. Together, the footholder assembly 102 and the leg rest 104 hold the foot and ankle relative to the leg during an installation procedure.

As FIG. 19 shows, the footholder assembly 102 is sized and configured for pivoting, under control of the physician, from a vertical or upright condition (shown in solid lines in FIG. 19) toward a more horizontal or tilted condition (shown in phantom lines in FIG. 19). In the upright condition, the assembly 102 serves to hold the ankle joint in a desired orientation with respect to the natural arterial-to-posterior and medial-to-lateral axes. By establishing and maintaining proper alignment of both the anterior/posterior and medial/lateral axes, the ankle replacement system 10 establishes and maintains proper stress distributions through the walking gait. The assembly 102 can be pivoted in a controlled fashion to cause flexion of the ankle joint, if and when desired during the installation procedure. The footholder assembly 102 can be locked by the physician in any desired orientation between the full upright condition and full pivoted condition.

Figure 20:
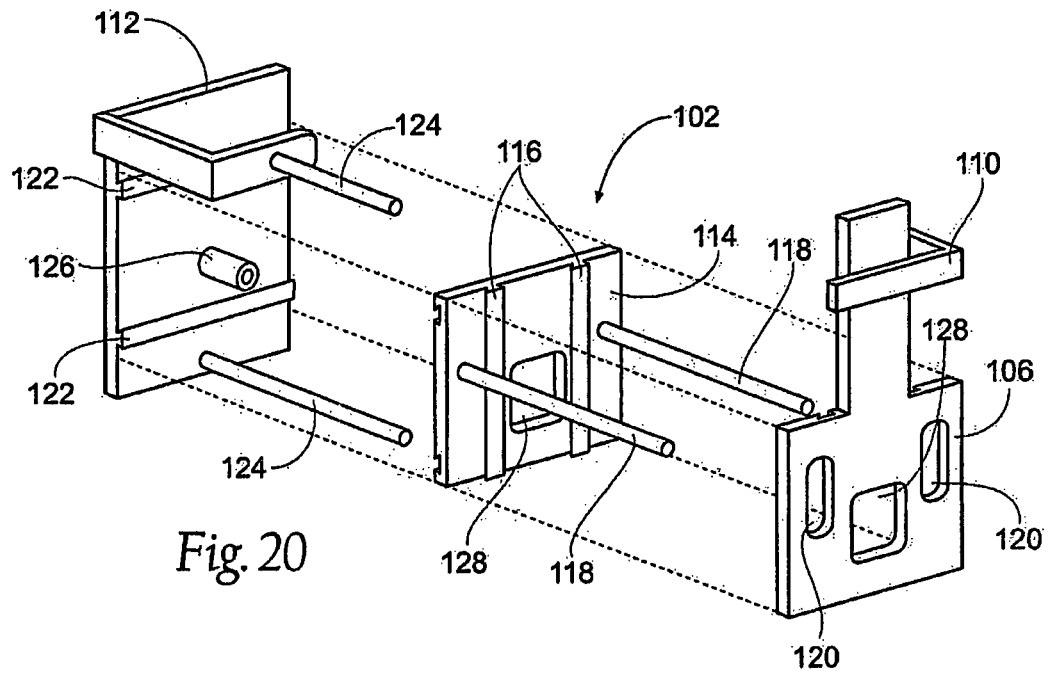
FIG. 20 is an exploded perspective view of a footholder assembly that forms a part of the alignment tool shown in FIG. 19.

The footholder assembly 102 also allows the ankle joint to be precisely oriented and maintained, using fluoroscopy, in a desired alignment with the major axis of the tibia. As FIG. 20 shows, the footholder assembly 102 includes, in addition to the foot rest 106, a back plate 112 and mid-plate 114, which is sandwiched between the foot rest 106 and the back plate 112.

Figure 21A:
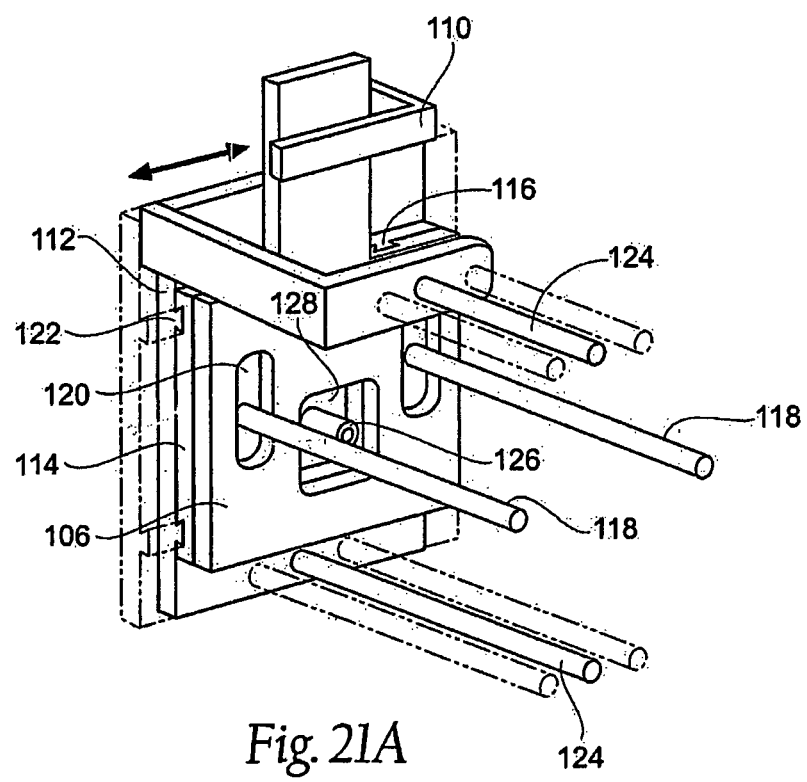

The mid-plate 114 is coupled to the foot rest 106 by sliding dovetail couplings 116 for up-and-down (vertical) movement relative to the foot rest 106. A pair of oppositely spaced alignment rods 118 is carried by the mid-plate 114. The alignment rods 118 lay in the same horizontal plane. The alignment rods 118 extend from the mid-plate through vertically elongated slots 120 in the foot rest 106, so that, in use (see FIG. 19) the rods 118 lay on opposite sides of the tibia in the medial-to-lateral plane. Vertical movement of the mid-plate 114 moves the alignment rods 118 up-and-down in unison within the slots 120 on opposite sides of the foot rest 106 (see FIG. 21B).

The back plate 112 is coupled to the mid-plate 114 by sliding dovetail couplings 122 for side-to-side (horizontal) movement relative to the foot rest 106. A pair of oppositely spaced alignment rods 124 is carried by the back plate 112. The alignment rods 124 lay in the same vertical plane. The alignment rods 124 extend from the back plate 112 above and below the foot rest 106, so that, in use (see FIG. 19) the rods 124 lay on opposite sides of the tibia in the anterior-to-posterior plane. Horizontal movement of the back plate 112 moves the alignment rods 124 side-to-side in unison above and below the foot rest 106 (see FIG. 21A).

The back plate 112 also carries a bushing 126. The bushing 126 extends through openings 128 in the mid-plate 114 and foot rest 106 and terminates at or near the plane of the foot rest 106 against which the bottom of the foot contacts. The center of the bushing 126 coincides with the intersection of the horizontal plane of the rods 118 and the vertical plane of the rods 124.

The rods 118 and 124 are made of materials that are visualized by fluoroscopy.

In use, the leg and foot are prepped for surgery. The physician desirably makes an anterior incision to gain initial access to the ankle joint. The foot and lower leg are placed in the foot rest 106 and leg rest 104. The physician estimates the ankle's axis of dorsi-plantar rotation and visually aligns the ankle to the axis of rotation of the alignment tool 100. The foot rest 106 is adjusted to rotate the foot so that the big toe is pointing essentially vertically. The forefoot and heel are secured to the foot rest 106 with the clamps 108 and 110 already described. The leg rest 104 is adjusted to the calf so that the tibia 16 is approximately parallel to the floor. The foot and calf are desirably aligned so that the anterior-posterior (A-P) line of the talus's trochlea is essentially vertical.

As shown in FIGS. 17A and 17B, a fluoroscopy unit 130 is aligned to the medial-lateral rods 118. When aligned, the rods 118 appear as one in fluoroscopy. The physician moves the mid-plate 114 to align the rods 118 to the center axis (Z-axis) of the tibia 16. Suitable manual or powered alignment controls (not shown) can be provided for this purpose. When the desired medial-to-lateral alignment of the rods 118 with the z-axis is accomplished, the mid-plate 112 is locked to the foot rest 106.

As FIGS. 18A and 18B show, the fluoroscopic unit 130 is moved ninety degrees to an anterior to posterior position. The fluoroscopy unit 130 is aligned to the anterior-to-posterior rods 124. When aligned, the rods 124 appear as one in fluoroscopy. The physician moves the back plate 112 to align the rods 124 to the center axis (Z-axis) of the tibia 16. Suitable manual or powered alignment controls (not shown) can be provided for this purpose. When the desired medial-to-lateral alignment of the rods 124 with the z-axis is accomplished, the back plate 112 is locked to the foot rest 106.

The pairs of rods 118 and 122 (respectively horizontal and vertical) are used in concert to minimize parallax with the fluoroscopy procedure. When the rods 118 and 122 both optically "blend" into one, signifying alignment, true horizontal or vertical alignment of the leg and ankle joint is achieved radiologically. For each pair of rods, one rod can be fashioned to be fluoroscopically distinguished from the other, e.g., one rod can be grooved, while the other is smooth.

Once centering is complete, all guide rods 118 and 124 can be removed to allow unobstructed surgical access to the ankle joint.

Figure 24:
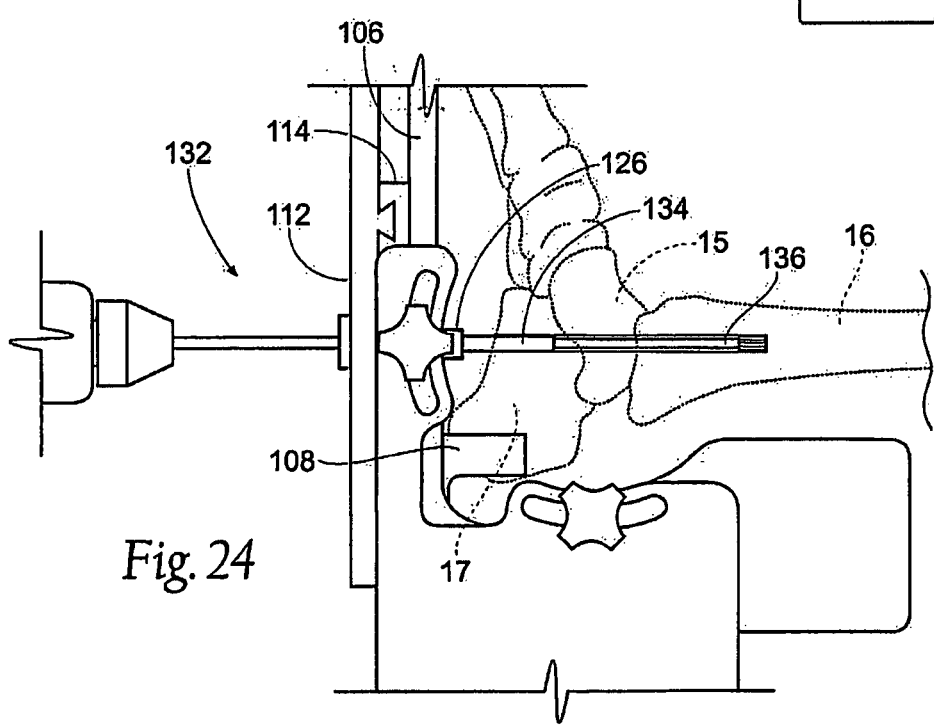
FIG. 24 is a side view of representative tools and methodologies, which serve the task of establishing an in-line intramedullary path through the calcaneus, talus, and tibia.
Figure 26:
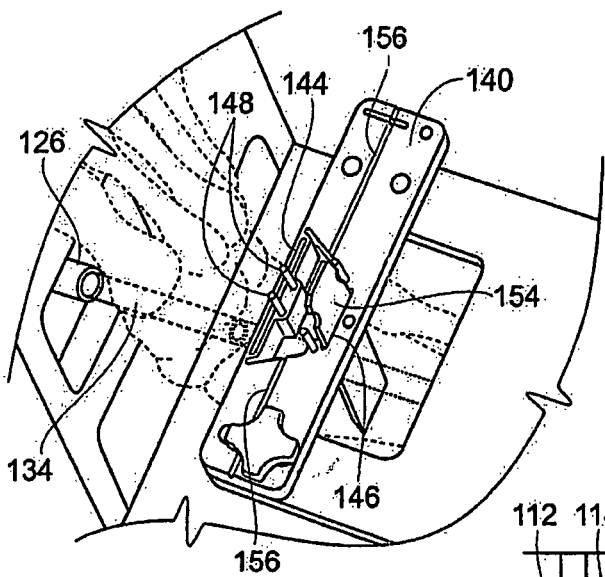
FIG. 26 is a top perspective view of the tools and methodologies shown in FIG. 25A in use to make bony cuts in the talus and tibia to clear a joint space for installation of the tibial and talar prosethesis platforms.

2. Establishing an in-line Intramedullary Path Through the Calcaneus, Talus, and Tibia FIG. 24 shows representative tools 132, and methodologies, which serve the task of establishing an in-line intramedullary path through the calcaneus, talus, and tibia. The tools 132 include a bottom foot cannula 134 which establishes an intramedullary guide path through the calcaneus and talus that leads into the tibia.

The bushing 126 on the back plate 112 is slaved to alignment with the axis of the tibia by alignment of the rods 118 and 124 to the same anatomic target. Thus, after using the alignment tool 100 as just described to align the ankle joint with the tibia, in line drilling of the center of the ankle and tibia for introduction of the bottom foot cannula 134 is made possible, because the bushing 126 has been aligned, by alignment of the rods 118 and 124, to achieve the desired line-drilling position up through the bottom of the foot.

There are various minimally invasive surgical techniques for introducing the bottom foot cannula 134. In one representative embodiment, the bushing 126 is temporarily separated from the back plate 112 (e.g., by unscrewing) to provide access to the bottom of the foot. The physician uses a scalpel to make an initial incision in the bottom of the foot, and the bushing 126 is replaced. A cannulated trocar loaded with a k-wire (not shown) can be inserted through the bushing 126, into the bottom of the foot, until the calcaneous 17 is contacted and the k-wire is firmly set into the calcaneous 17. The trocar can then be removed, and the k-wire lightly tapped further into the calcaneous 17. In a representative embodiment, the bushing 126 measures 6 mm in diameter, and the cannulated trocar can be 6 mm loaded with a 2.4 mm k-wire. The physician can now operate a cannulated first reamer (e.g., 6 mm) (not shown) over the k-wire up into the calcaneous 17 and talus 15 approximately 30 mm. The first reamer opens an access path for insertion of the bottom foot cannula 134.

Withdrawing the first reamer and bushing 126, the physician can now insert the bottom foot cannula 134 (as shown in FIG. 24). With the bottom foot cannula 134 in place, a second reamer 136 (e.g., 5 mm) can be operated through the cannula 134 to drill approximately another 100 mm through the talus 15 and up into the tibia 16. Fluoroscopy may be used, if desired, to verify the accuracy of the drilled hole.

An intramedullary guide path has been established through the calcaneus and talus leading into the tibia. The presence of the bottom foot cannula 134 maintains the guide path in alignment with the axis of the tibia.

3. Establishing Anterior Access and Making Bony Cuts in the Talus and Tibia

FIGS. 25A, 25B, 25C and FIG. 26 show representative tools 138 and methodologies, which serve the purpose of establishing anterior access to the ankle joint for the purpose of making bony cuts in the talus and tibia to install the tibial and talar platforms 12 and 20.

In the representative embodiment, the tools 138 include a cutting guide fixture 140 which is installed and stabilized over the ankle joint in an anterior position to the ankle joint. The cutting guide fixture 140 is secured to an underlying frame 142 to which the alignment tool 100 is also attached.

As FIG. 25A shows, the cutting guide fixture 140 includes a superior bone cutting blade guide 144 and an inferior bone cutting blade guide 146.

The cutting guide fixture 140 also includes apertures for receiving fixation pins 148 adjacent the blade guides 144 and 146. In a representative embodiment, the pins 148 can comprise 2.4 mm Steinmann pins. A pair of the pins 148 are drilled adjacent the superior blade guide 144 into the tibia 16, and the other pair of the pins 148 are drilled into the talus 15 adjacent the inferior blade guide 146. To maximize operating field space, the pins 148 may be cut flush at the fixture 140, if desired. The operating field of the ankle joint is thereby stabilized, as shown in FIG. 25A.

As FIG. 25A also shows, the cutting guide fixture 140 also includes an aperture 150 for establishing an anti-rotational notch. The physician can form the anti-rotational notch, e.g., by using a drill and lock collar (e.g. 4 mm) operated through the aperture. As FIG. 25A shows, using fluoroscopy, the bottom foot cannula 134 is kept in the foot, but out of the way of superior blade guide 144 and the intended location of the anti-rotation notch 150.

When establishing the anti-rotational notch, the physician desirably notes from the drill the approximate depth of the underlying bone. On the superior and inferior saw blades 152 and 154 (see FIGS. 20B and 20C), the physician notes the depth required based upon the previously measured drill depth.

As FIG. 25B shows, the superior saw blade 152 is operated through the superior blade guide 144 to cut the top surface of the tibia 16.

Retaining the bottom foot cannula 134 within the foot while making bony cuts results an enhanced level of accuracy, because there is essentially no relative movement of the joint components during the drilling and sawing operations. Considerable force is often exerted upon the joint during drilling and sawing operations, which can move the joint out of the desired orientation for optimal prosthesis placement. The bottom foot cannula 134 helps ensure the joint components maintain the correct alignment relative to one another so that the resulting cuts are more accurately positioned.

Using fluoroscopy, the bottom foot cannula 134 is then retracted out of the way of inferior blade guide 146 (see FIG. 25C). As FIGS. 20C and 21 show, the inferior saw blade 154 is operated through the inferior blade guide 146. The bottom surface of the talus 15 is cut to the depth previously noted.

The bottom foot cannula 134 is reinserted into the foot and both sides of the joint space are cut using side saw blade guide slots 156 (see FIG. 25A).

Figure 27A:
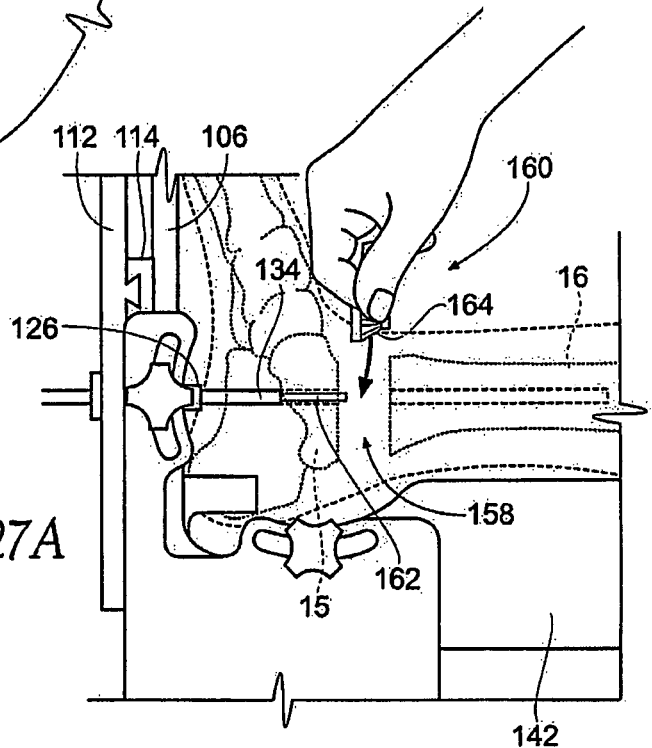
FIGS. 27A and 27B are side views of representative tools and methodologies, which serve the purpose of establishing an intramedullary passage within the tibia, into which the stem component of the tibial platform can be installed, making use of anterior access through the cleared joint space formed using the tools and methodologies of FIGS. 25A, 25B, 25C, and 26.

The fixture 140 and pins 148 can now be removed. With a rounded osteotome, the corner of the joint space is cut out. The sides of the anti-rotation notch are cleaned so' that the sides are essentially vertical. Loose bone pieces are removed and the cleared joint space irrigated. FIG. 27A shows the cleared joint space 158 and the anterior access it provides for the insertion of other installation tools and the components of the tibial and talar platforms 12 and 20.

4. Creating Passages for Stem Components

In the illustrated embodiment, both tibial and talar platforms 12 and 20 include respective stem components. As previously described, these stem components provide enhanced fixation and support to the platforms. The creation of the passages for installation of these stem components in the tibia and talus will now be described.

a. Boring the Tibia for the Tibial Stem

Figure 27B:
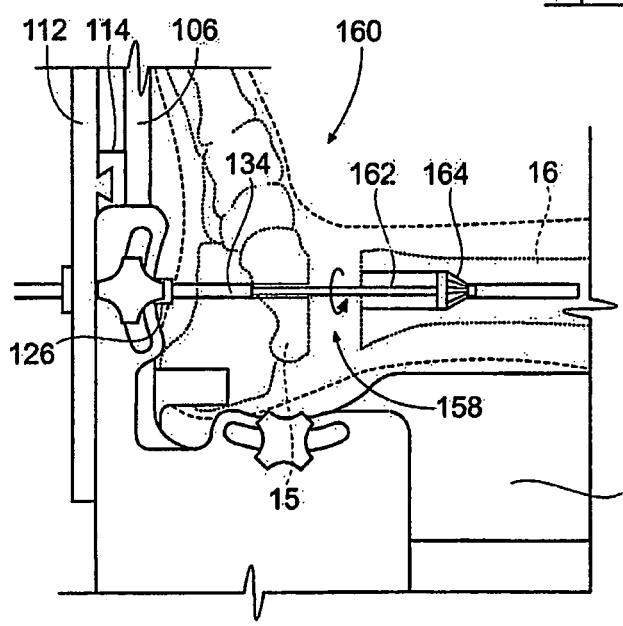

FIGS. 27A and 27B show representative tools 160 and methodologies, which serve the purpose of establishing an intramedullary passage within the tibia, into which the stem component of the tibial platform 12 can be installed, making use of anterior access through the cleared joint space 158.

In the representative embodiment, the tools 160 include a tibial stem driver 162 having a threaded end and a tibial stem reamer 164, which can be removably screwed onto the threaded end of the driver 162. The installation of the bottom foot cannula 134 (previously described) makes its possible to couple of the reamer 164 to the driver 162 using the anterior access that the cleared joint space 158 provides. As shown in FIG. 27A, the threaded end of a tibial stem driver 162 can be inserted through the bottom foot cannula 134 to the cleared joint space 158. As FIG. 27A shows, the physician has open anterior access here to insert the tibial stem reamer 164 into the cleared joint space 158 and to screw the reamer 164 onto the driver 162.

The reamer 164 desirably includes a bullet-shaped nose that fits within the previously formed 5 mm passage in the tibia 16. Entering the passage, the reamer 164 enlarges the intramedullary tibial passage, as FIG. 27B shows. A depth mark can be noted on the driver 162 so that the tibia 16 is reamed for another approximately 70 mm, as FIG. 27B shows.

The physician can retract the driver 162 and the reamer 164 through bottom foot cannula 134 to expose the reamer 164 with the joint space 158. There, the physician can unscrew the reamer 164 from the driver 162 to withdraw the reamer 164 through the anterior access. The driver 162 can be withdrawn from the bottom foot cannula 134.

The intramedullary passage for installation of the tibial stem has thereby been established.

b. Boring of the Talus and Calcaneus for the Calcaneal Stem

FIGS. 28A to 28D show representative tools 166 and methodologies, which serve the purpose of establishing a talar-calacaneal passage bridging the talus and calcaneus. The stem component of the talar platform 20 can be installed in the talar-calacaneal passage. The tools 166 and methodologies operate by anterior access through the previously-cleared joint space 158.

Figure 28A:
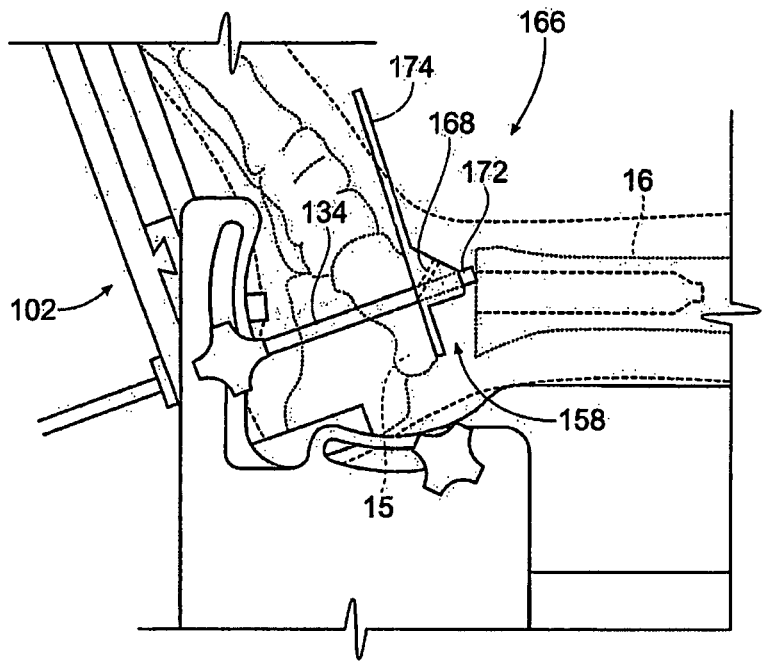
FIGS. 28A to 28E show in perspective views representative tools and methodologies, which serve the purpose of establishing a talar-calacaneal passage bridging the talus and calcaneus, in which the stem component of the talar platform 20 be installed making use of the anterior access through the cleared joint space formed using the tools and methodologies of FIGS. 25A, 25B, 25C, and 26.
Figure 28B:
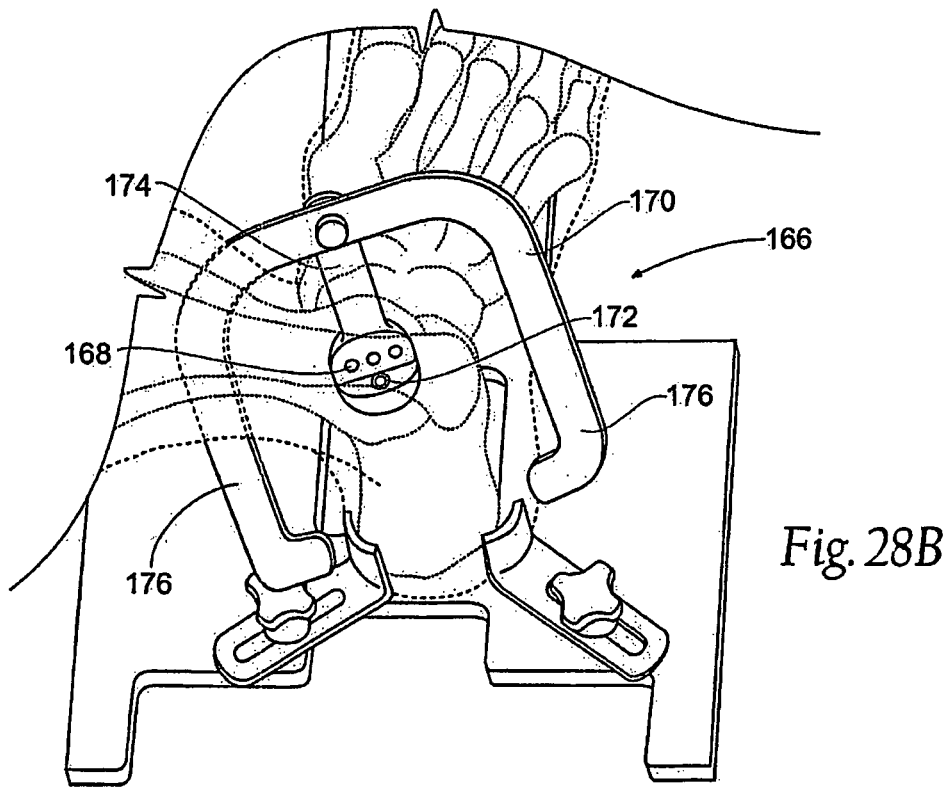

In the representative embodiment, the tools 166 include a calcaneal drill pin fixture 168 (FIG. 28A) and a companion calcaneal orientation fixture 170 (FIG. 28B). The drill pin fixture 168 establishes the anterior-to-posterior drill angle for formation of the talar-calcaneal passage, into which the calcaneal stem is eventually installed. The orientation fixture 170 couples to the drill pin fixture 168 to aid in establishing a desired medial-to-lateral orientation of the drill path.

Prior to use of the drill pin fixture 168 (see FIG. 28A), the footholder assembly 102 is pivoted out of its upright condition to rotate the foot to maximum plantar flexion. As FIG. 28A shows, the drill pin fixture 168 is installed into the flexed open joint space 158. An orienting pin 172 is slid up the bottom foot cannula 134 and joined to an aperture in the pin fixture 168. With the orientation pin in place, the bottom foot cannula 134 can be withdrawn.

The orientation fixture 170 is coupled to the pin fixture 168 (as FIG. 28B shows). In the illustrated embodiment, the drill pin fixture 168 includes an appendage 174 over which the orientation fixture 170 removably fits. The orientation fixture 170 includes a symmetrical array of medial-lateral side arms 176, which sweep in a curved path into a spaced apart facing relationship at their terminal ends. Grasping the arms 176, the fixture 170 can be manipulated side-to-side or rotationally. Such movement of the orientation fixture imparts comparable movement to the pin fixture 168, thereby changing the medial-to-lateral orientation of the pin fixture 168 with respect to the calcaneus. The orientation fixture 170 is manipulated to place the terminal ends of the arms 176 in an equally spaced orientation on either side of the calcaneous 17.

Figure 23A:
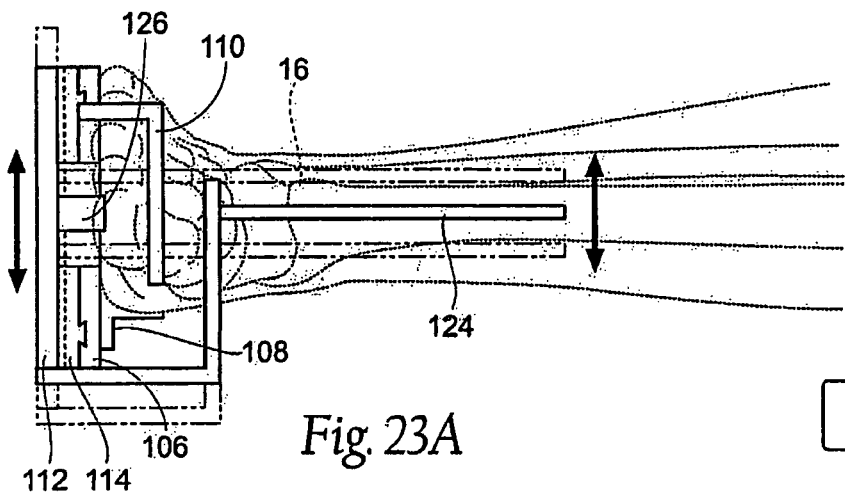
FIGS. 23A and 23B are, respectively, top and end views of the footholder assembly shown in FIGS. 21A and 21B, showing the range of horizontal movement that makes possible horizontal alignment of the leg and ankle joint radiologically.
Figure 23B:
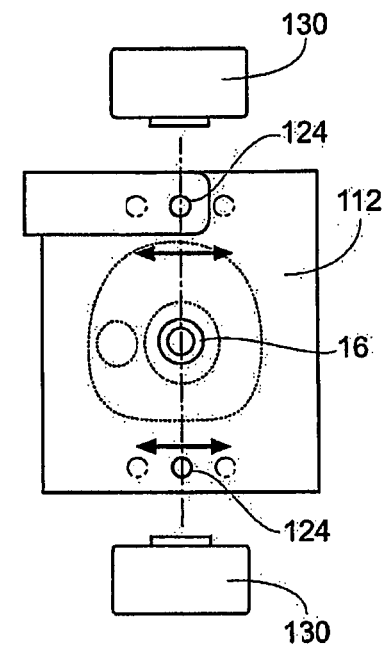

As shown in FIG. 23C, once the pin fixture 168 has been oriented, a pair of fixing pins 178 are inserted into side holes pin fixture 168, to secure the pin fixture to the talus 15.

Figure 28C:
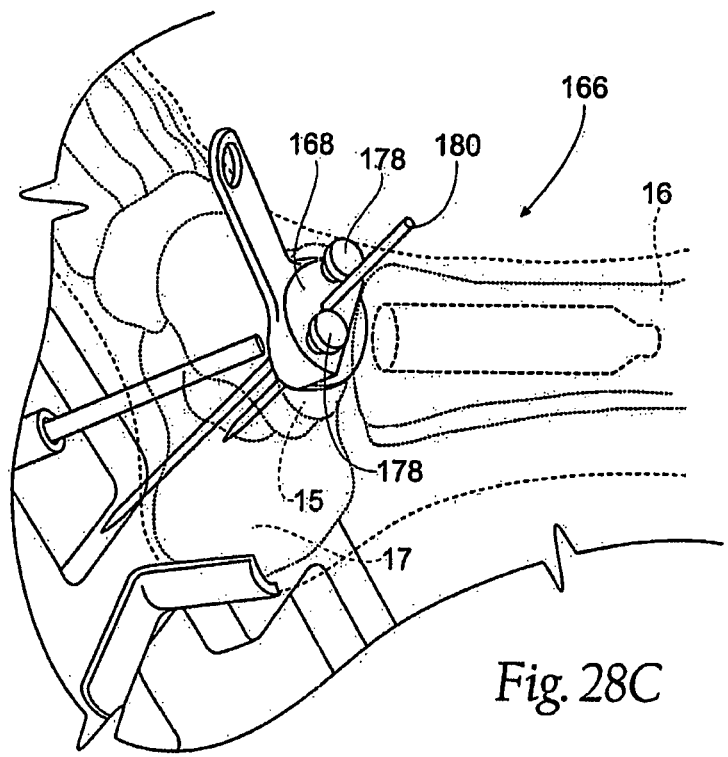

As FIG. 28C also shows, the physician drills a guide pin 180 into the center hole of the pin fixture 168, approximately 65 mm into the calcaneus 17. In a representative embodiment, the pin 160 comprises a 2.4 mm Steinmann pin. The fixing pins 178 and the pin fixture 168 can now be removed, leaving the guide pin 180 in the calcaneous 17.

Figure 28D:
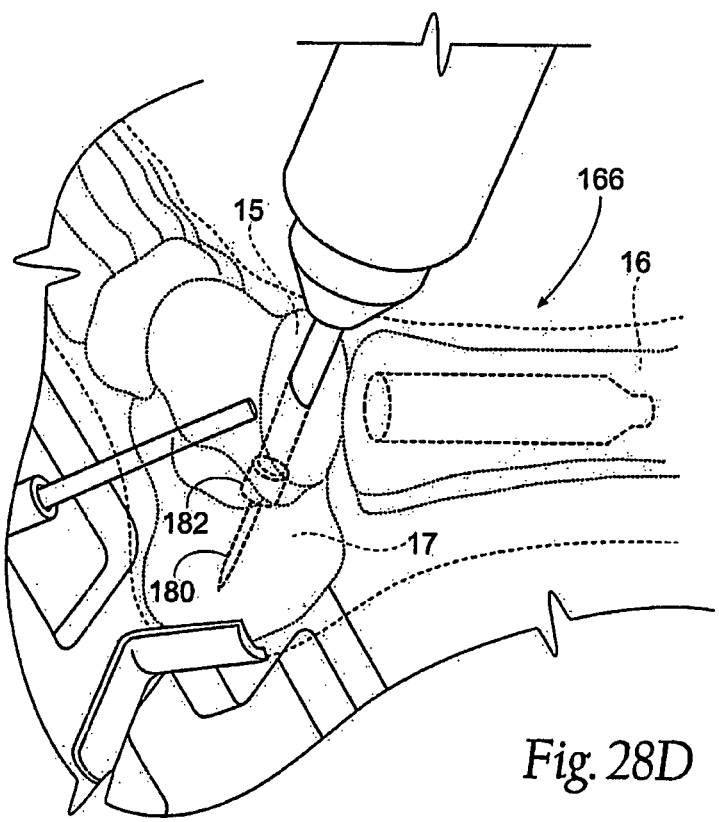
Figure 28E:
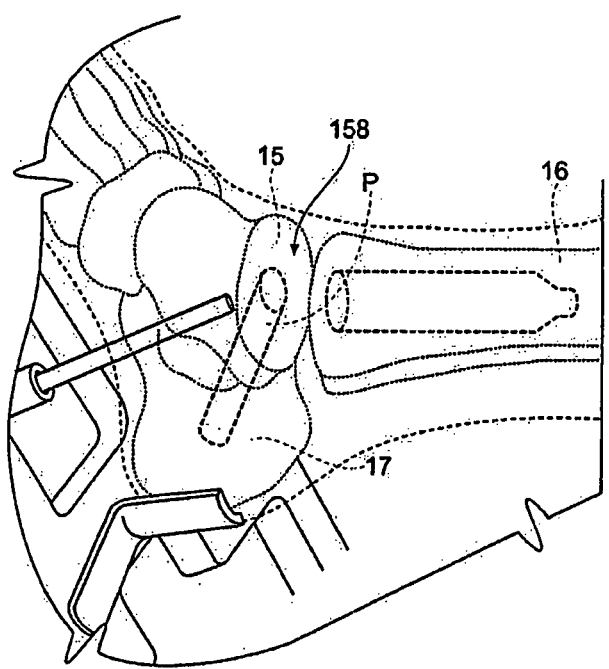

As FIG. 28D shows, a calcaneal reamer 182 is inserted over the guide pin 180 and advanced approximately 65 mm into the calcaneous 17. The calcaneal reamer 182 is withdrawn, leaving the formed passage P (see FIG. 28E) into which the calcaneal stem will eventually be inserted.

The footholder assembly 102 is pivoted back to its original upright position. The bottom foot cannula 134 is reinserted.

In this representative way, the trans-talar-calcaneal passage for installation of the calcaneal stem can be established.

5. Installing the Tibial Stem and Platform

FIGS. 29A to 29D and FIG. 30 show representative tools 184 and methodologies, which serve the purpose of installing the tibial stem 30 and platform 12.

In the illustrated embodiment, the tibial platform 12 is secured within the tibia 16 by a multi-piece stem 30 of the type previously described, as is shown in FIGS. 4A and 4B. In an earlier described installation sequence, and as shown in FIGS. 27A and 27B, an intramedullary passage has been previously formed within the tibia to receive the multi-piece stem component 30.

In this installation sequence, as in previously described sequences of the installation, installation of the multi-piece stem component 30 takes advantage of the anterior access provided to the cleared joint space 158, as well as the calcaneal access provided by the bottom foot cannula 134.

Figure 29A:
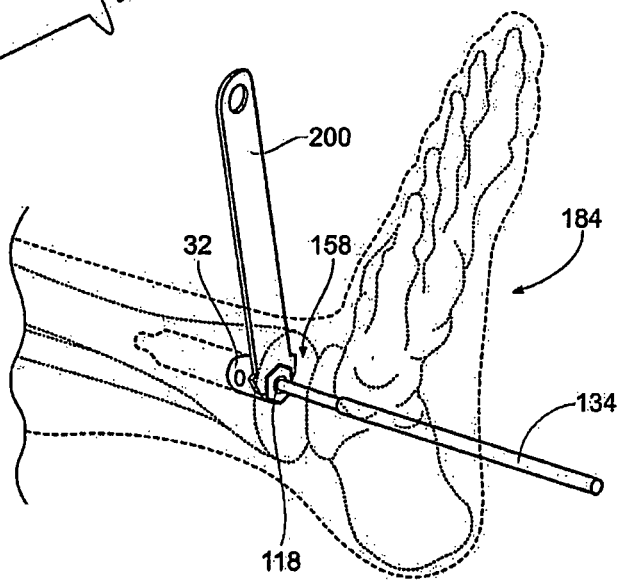
FIGS. 29A to 29D and FIG. 30 show in perspective views representative tools and methodologies, which serve the purpose of installing the multi-piece tibial stem (as also shown in FIGS. 4A and 4B) and platform, the stem being assembled in situ in the intramedullary passage formed within the tibia formed using the tools and methodologies shown in FIGS. 27A and 27B.

As FIG. 29A shows, the physician inserts the top tibial stem component 32 into the joint space 158 through the previously formed anterior access. The tools 184 include a wrench 200 or other suitable tool. The wrench 200 engages the exterior stem flats of the top stem component 32, gripping the top stem component 32. The top stem component 32 is advanced partially up into the preformed tibial passage. The wrench 200 abuts against the cut tibial bony surface, checking the advancement of the top stem component 32 beyond the superior confines of the cleared joint space 158.

Figure 29B:
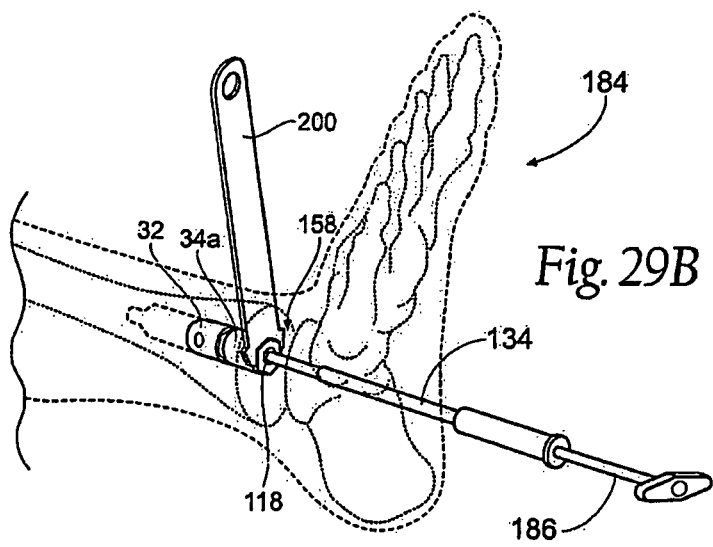

As shown in FIG. 29B, a mid stem component 34A, is inserted through the anterior incision. The tools 184 includes an intramedullary driver 186 that is advanced through the bottom foot cannula 134 into the cleared joint space 158. The driver 186 includes a male hex fitting 188 at its distal end. The hex fitting 188 of the driver 186 mates with the internal female hex 38 inside the mid stem component 34A (the internal female hex 38 is shown in FIG. 4A). With the wrench 200 engaging the top stem component 32 to keep it from rotating, the physician twists the driver 186 to torque the threaded male end of the mid stem component 34A into the threaded female end of the top stem component 32. This joins the top and mid stem components 32 and 34A. Once tightened, the wrench 200 is switched from the top stem component 32 to the stem flats of the mid stem component 34A. The physician axially advances the driver 186 to push the top stem component 32 beyond the confines of the cleared joint space 158 and up into the tibial passage.

Figure 29C:
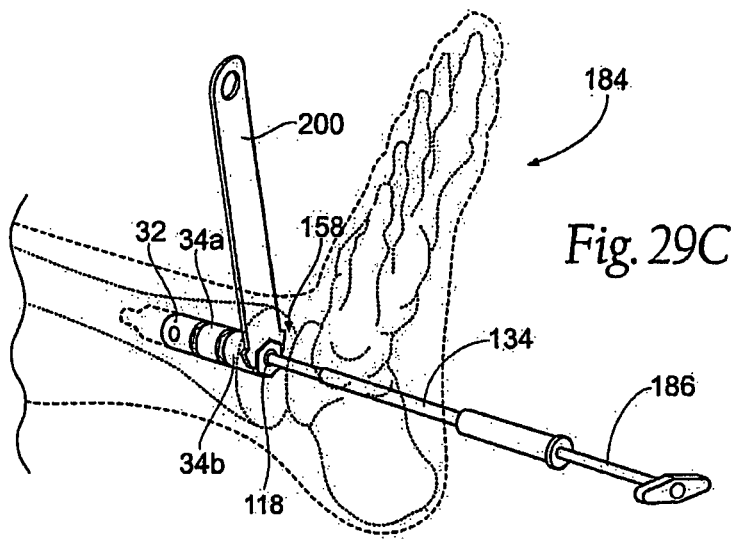

As FIG. 29C shows, the hex fitting 188 is withdrawn from the mid stem piece 34A, and the driver 186 is withdrawn sufficient to permit the insertion of a second mid stem component 34B through the anterior access into the joint space 158. The sequence just described is repeated. The hex fitting 188 of the driver 186 mates with the internal female hex 38 inside the second mid stem component 34B. With the wrench 200 engaging the first mid stem component 34A to keep it from rotating, the physician twists the driver 186 to torque the threaded male end of the second mid stem component 34B into the threaded female end of the first mid stem component 34A. Once tightened, the wrench 200 is switched to the stem flats of the second mid stem component 34B. The physician axially advances the driver 186 to push the first mid stem component 34A, proceeded by the top stem component 32, beyond the confines of the cleared joint space 158 and up into the tibial passage.

Additional mid stem components can be installed in this fashion, depending upon the intended final length of the stem 30.

Figure 29D:
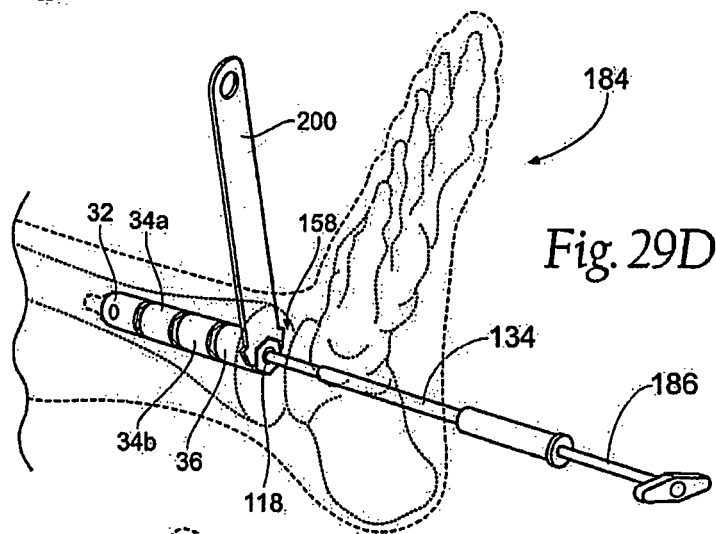

In turn, when insertion of a bottom stem component 36 is desired (this component is shown in FIG. 4A), the hex fitting 188 is withdrawn from the then end-most assembled stem piece. The driver 186 is withdrawn sufficient to permit the insertion of the bottom stem component 36 into the anterior incision. As FIG. 29D shows, the hex fitting 188 of the driver 186 engages the internal female hex 38 inside the bottom stem component 36. With the wrench 200 engaging the end-most assembled stem component (shown for purpose of illustration to be the second mid stem component 34B), the physician twists the driver 186 to torque the threaded male end of the bottom stem component 36 into the threaded female end of the first mid stem component 34A. The wrench 200 is switched to the flats of the bottom stem component 36. Using the driver 186, the physician axially advances the assembled multi-piece stem 30 into the tibial passage, beyond the confines of the cleared joint space 158.

In an alternative arrangement, the bottom stem component 36 need not have an internal hex, in which case the bottom stem component 36 may be torqued onto the then end-most assembled stem piece using a threaded driver or other suitable tool inserted into the joint space 158.

Figure 30:
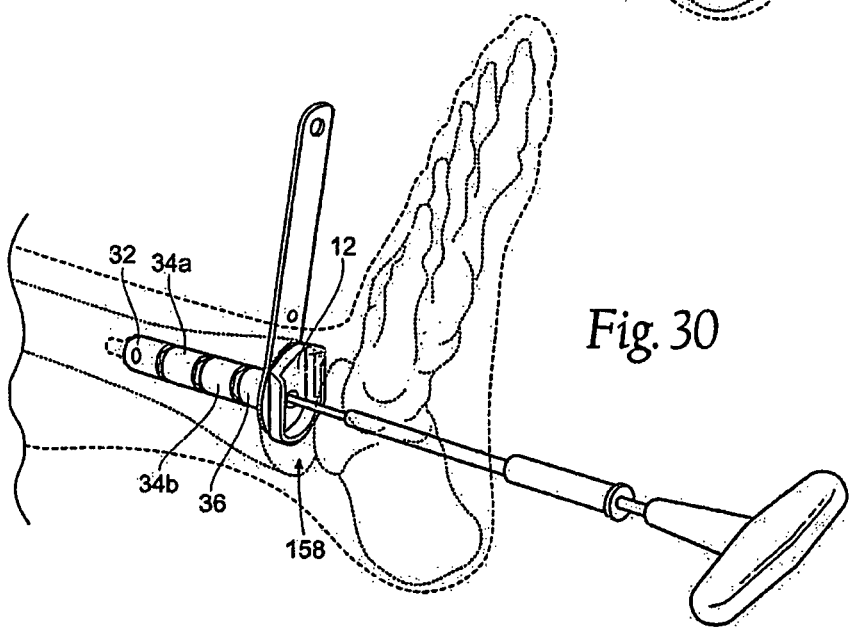

As FIG. 30 shows, holding the bottom stem component 36 with the wrench 200, the physician inserts a tibial platform 12 into the joint space. The physician uses the driver 186, advanced through the bottom foot cannula 134 to couple the tibial platform 12 to the bottom stem component 36, e.g., by inserting a male Morse fitting on the platform 12 into a corresponding female fitting on the bottom stem component 36.

If desired, the platform 12 may be marked for easy placement reference. For example, the face may be marked ANT-R (for the right foot or ANT-L, for the left foot) to clearly indicate that the face is placed facing anterior (not shown).

If desirable, bone cement may be applied to the top of the tibial platform 12. The platform 12 is then firmly pushed against the bottom of the tibia 16 to push the stem 30 firmly into the tibia 16 and the anti-rotation notch 150.

6. Assembly and Installation of the Talar/Calcaneal Stem and Talar Artificial Joint Surface As previously described, FIGS. 28A to 28E show representative tools 166 and methodologies, which serve the purpose of establishing a passage P bridging the talus and calcaneus (see FIG. 28E), into which the stem component 26 of the talar platform 20 is installed.

Figure 31:
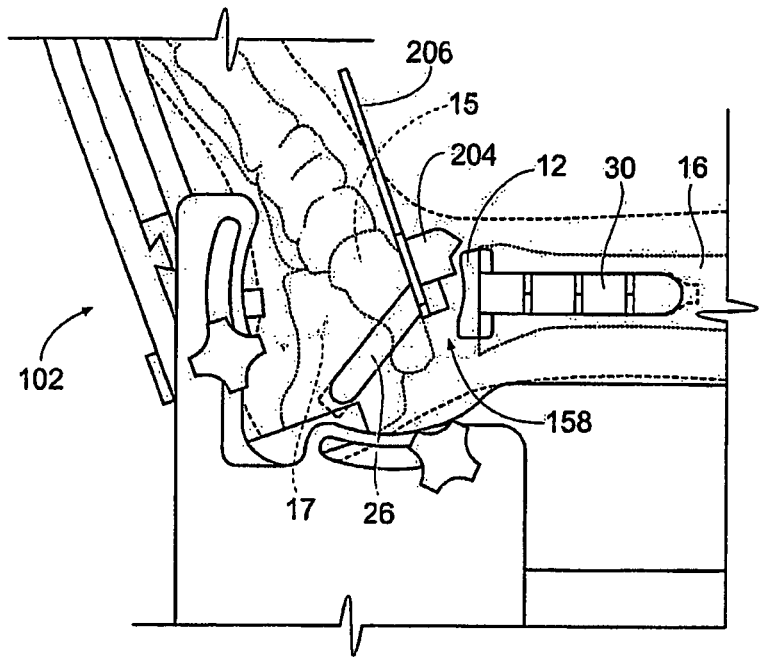
FIG. 31 shows in a side view the installation of the calcaneal stem component into the passage bridging the talus and calcaneus (see FIG. 28E) formed using the tools and methodologies shown in FIGS. 28A to 28E.

FIG. 31 shows the installation of the calcaneal stem component 31 into the passage P.

As FIG. 31 shows, the footholder assembly 102 is pivoted out of its upright condition to rotate the foot to maximum plantar flexion. The physician selects the appropriate angled talar/calcaneal stem 26. The stem 26 is inserted into the previously formed passage P in the talus 15 and calcaneous 17.

A strike block assembly 204 is placed over the proximal end of the stem 26. A protective cover (not shown) may be provided for the proximal end of the stem 26, in which case the strike block assembly 204 is placed over the cover. The block assembly 204 is struck to seat the stem 26 firmly into the talus 15 and calcaneous 17.

It is desirable that the orientation of the stem 26 and block 204 be essentially parallel to the surface of the talus 15. A wrench 206 or other suitable tool may be used to adjust the orientation if necessary. The stem 26 is struck until the block 204 is flush to the surface of the talus 15. The stem cover (if used) is then removed.

Figure 32:
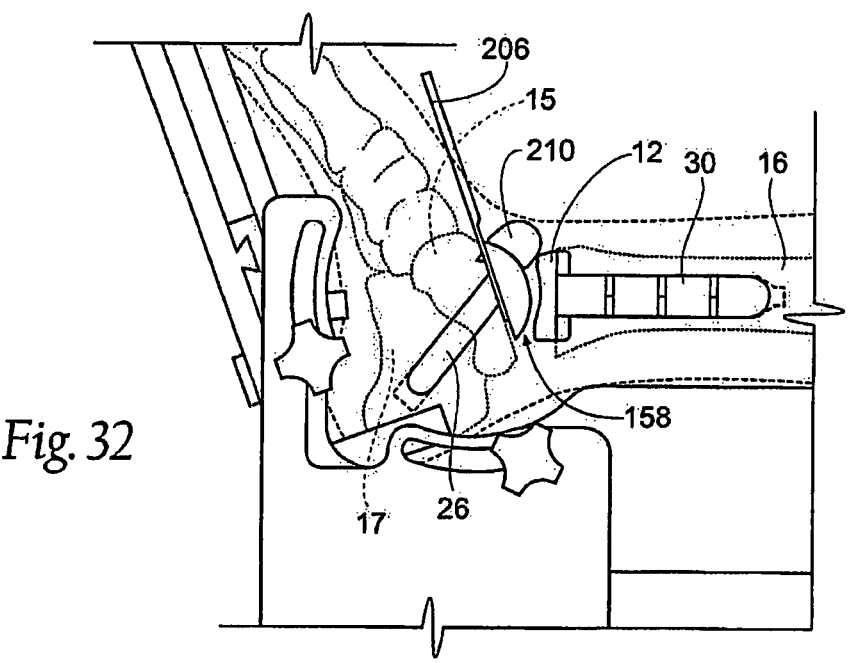
FIG. 32 shows in a side view the placement of the talar artificial joint surface on the calcaneal stem component installed using the tools and methodologies shown in FIG. 31.

As FIG. 32 shows, the wrench 206 is placed under the fitting 208 on the proximal end of the stem 26. The physician places the talar artificial joint surface 24 on the stem 26 in the desired orientation. Bone cement may be applied to the bottom surface of the talar artificial joint surface 24 if desired. The surface 24 is set onto the stem 26 by striking a strike block 210 with a mallet or other suitable tool (not shown). The block 210 then struck until the bottom of the surface 24 is seated flush on the surface of the talus 15. The wrench 206 may then be removed.

7. Insertion of the Tibial Artificial Joint Surface

The physician next determines the optimal tibial artificial joint surface 22 using sizing blocks (not shown).

Figure 33:
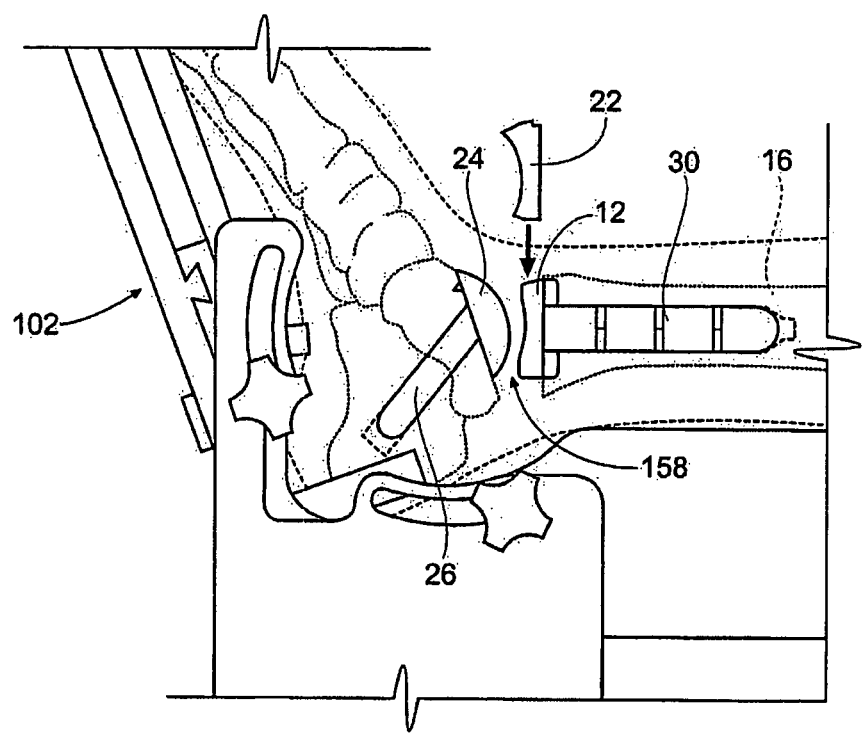
FIG. 33 shows in a side view the installation of the tibial artificial joint surface on the platform installed using the tools and methodologies shown in FIGS. 29A to 29D and FIG. 30.

As shown in FIG. 33, with the foot placed in plantar flexion, and the surface 22 is placed into the tibial platform 12, as represented by the arrow. If desired, the surface 22 may be marked for easy placement reference. For example, the face may be marked MED-R (for the right foot or MED-L for the left foot) to clearly indicate that the marking should be on the medial side of the surface 22 (not shown).

The foot is then checked for proper articulation. The incisions may then be irrigated and closed.

a. A Representative Installation Platform

Figure 34:
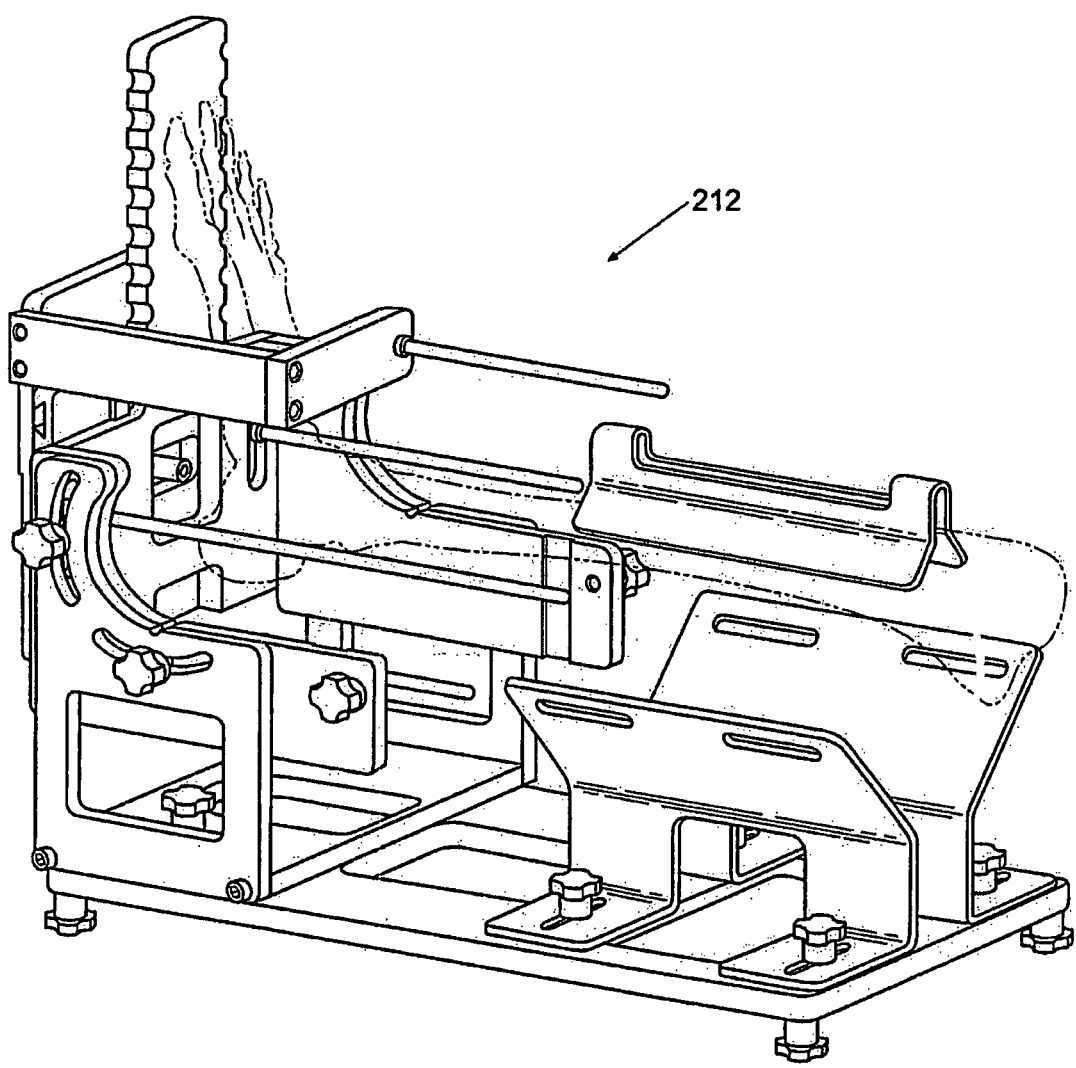
FIG. 34 is a left side perspective view of a representative installation platform to which a variety of jigs, fixtures, reamers, and auxiliary platforms of the form, fit, and function shown in FIGS. 19 to 33 may be rigidly and simply affixed to the sequence of tasks, including (i) the alignment of the ankle joint with the tibia, (ii) the establishing of an in-line intramedullary path through the calcaneus, talus, and tibia; (iii) the establishing of anterior access for the purpose of making properly oriented bony cuts in the talus and tibia to install the tibial and talar platforms; and (iv) the installation of the tibial and talar platforms.
Figure 35:
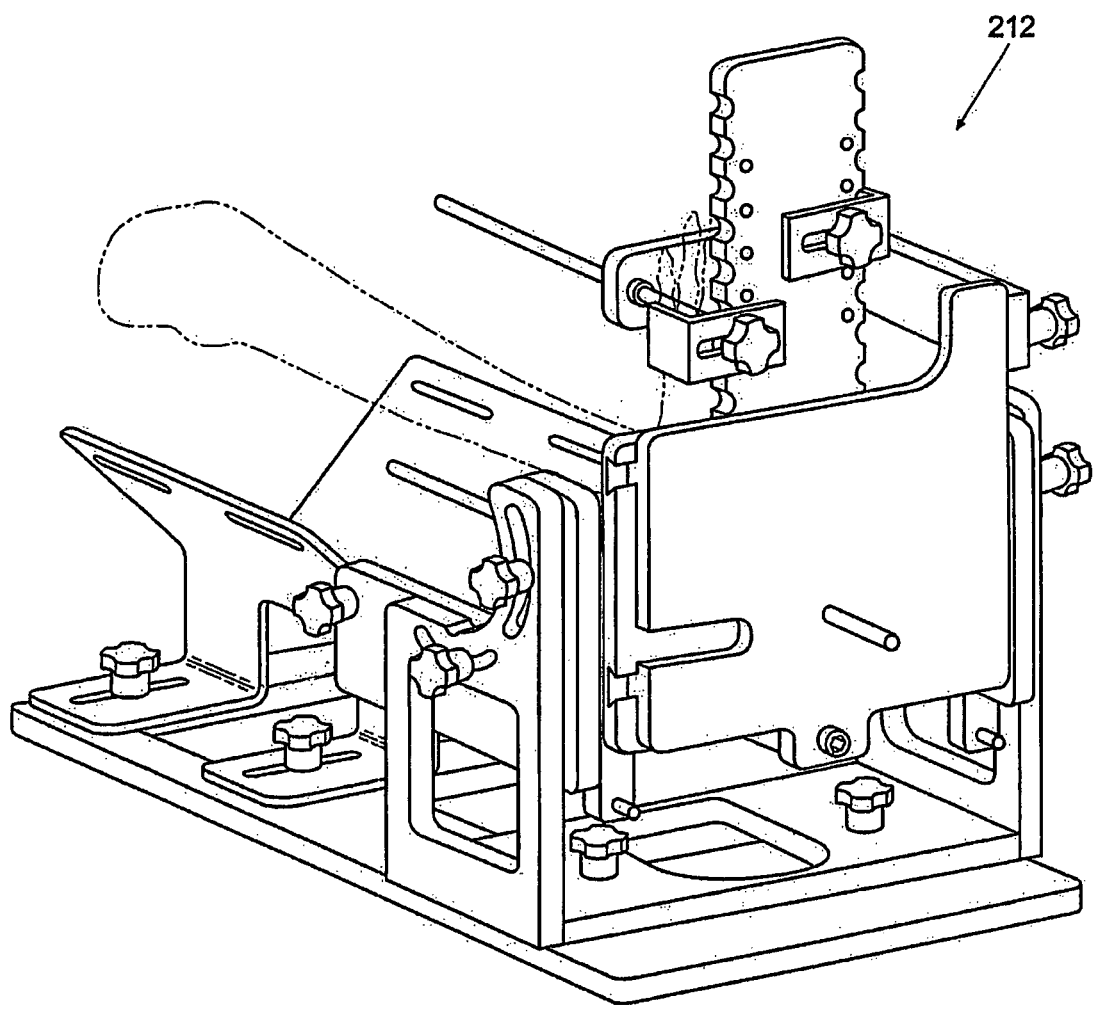
FIG. 35 is a right side perspective view of the installation platform shown in FIG. 34.

FIGS. 34 and 35 show a representative main installation platform 212 to which a variety of jigs, fixtures, reamers, and auxiliary platforms of the form, fit, and function just described, may be rigidly and simply affixed. These jigs, fixtures, reamers, and auxiliary platforms have the form, fit, and function to accomplish the sequence of tasks, as described, including (i) the alignment of the ankle joint with the tibia, (ii) the establishing of an in-line intramedullary path through the calcaneus, talus, and tibia; (iii) the establishing of anterior access for the purpose of making properly oriented bony cuts in the talus and tibia to install the tibial and talar platforms 12 and 20; (iv) the installation of the tibial and talar platforms 12 and 20. Preferably, these jigs, fixtures, reamers, and auxiliary platforms are removable as desired, to allow unobstructed surgical access to the ankle joint. The main installation platform 212 is desirably designed to facilitate cleaning and sterilization for re-use, though some parts may be acceptable for single use only.

The design of the main installation platform 212 is such that a fall range of leg sizes may be accommodated through a series of adjustments, with final alignment achieved with fluoroscopy, as will be described later.

b. Removal of the Prosthesis

The described devices and methods provide for easy replacement of the prosthesis should it be necessary or desirable.

The previously made incision is reopened and the foot is placed in plantar flexion. The talar artificial joint surface 24 is removed by prying from underneath with a flat screwdriver or other suitable tool. In some instances, the joint may need to be distended (e.g., about 3 mm) to remove the surface 24. If necessary, a small hole may be drilled in the surface 24 and a screw placed into the hole to aid in the removal. The calcaneal stem can then be loosened and removed with pliers.

To remove the tibial component, the bottom foot cannula is reinserted. Remove the tibial tray, and then insert the hex drive through the bottom foot cannula and sequentially unscrew and remove the stem pieces.

Technical features have been disclosed that include, singly or in combination:

(1) A multi-piece stem component (see, e.g., FIG. 4A) suitable for use in any surgical procedure in which a stem is required for fixation of an implant, whether it is a total joint implant, fusion (arthrodesis) implant, osteotomy fixation implant, or fracture fixation implant. The multi-piece stem component configuration is ideally suited for securing bone components together in a minimally invasive procedure, in which a small surgical opening is used to install large components. Two or more small stem components can be sequentially attached to one another in situ (see FIG. 4B) to make a larger stem assembly. Representative tools and methodologies for installing a multi-piece stem component are shown in FIGS. 29A to 29D.

(2) Articulating artificial joint surfaces (see, e.g., FIG. 6) comprising complementary ball-and-socket surfaces that not only articulate, but also allows the artificial joint to rotate about an axis. This makes possible more uniform wear of the surfaces to maximize function and longevity of the prostheses.

(3) Articulating artificial joint surfaces (see, e.g., FIGS. 7A, 7B, and 7C) comprising complementary ball-and-socket surfaces that not only articulate and rotate about an axis, but also accommodate fore and aft and lateral translation of the mating joint surfaces relative to the native bone.

(4) Artificial articulating joint surfaces (see, e.g., FIG. 8A), each of which comprises a saddle-shaped component. The saddle shape is geometrically characterized as a swept arc, comprising a surface defined by a first arc that is swept along a second arc that is perpendicular to the first arc. The geometry forms, for each surface, an elongated trough that curves along an axis.

(5) A prosthesis supporting an artificial joint surface that can be assembled in a snap fit and/or interlocking fashion that provides positive locking means without the use of screws or other fasteners (see, e.g., FIGS. 9, 10, 12A, and 13).

(6) A prosthesis accommodating fitment of a plastic joint surface made, e.g., from ultra high molecular weight polyethylene.

(7) An ankle replacement system that can be installed using minimally invasive intramedullary guidance established with respect to the major axis of the tibia by minimally invasive access through the calcaneus, through an incision in the bottom of the foot. Intramedullary guidance along the axis of the tibia makes it possible to make properly oriented bony cuts of the talus and tibia through anterior access to the ankle joint. Proper overall alignment of the total ankle system is achieved in desired alignment and orientation with all the natural axes of the native ankle joint it replaces, and improved long term results are achieved.

(8) Prostheses, tools, and methodologies that make possible the installation of a total ankle system using minimally invasive intramedullary guidance established with respect to the major axis of the tibia.

(9) Prostheses, tools, and methodologies that make possible the installation of a total ankle system using minimally invasive intramedullary guidance established with respect to the major axis of the tibia using fluoroscopic visualization.

(10) Prostheses, tools, and methodologies that make possible the installation of a total ankle system using minimally invasive anterior access to the ankle joint for making bony cuts and to install prosthesis components.

(11) Prostheses, tools, and methodologies that make possible the establishment of an in-line intramedullary path through the calcaneus, talus, and tibia.

Other embodiments and uses of the inventions described herein will be apparent to those skilled in the art from consideration of the specification and practice of the inventions disclosed. All documents referenced herein are specifically and entirely incorporated by reference. The specification should be considered exemplary only with the true scope and spirit of the invention indicated by the following claims. As will be easily understood by those of ordinary skill in the art, variations and modifications of each of the disclosed embodiments can be easily made within the scope of this invention as defined by the following claims.

What is claimed is:

1. A prosthesis, comprising:
   a prosthesis stem, including:
      a first stem component sized and configured to be installed in an intramedullary path, the first stem component including a first external feature including at least two flats disposed at a first internally threaded female end, the first internally threaded female end disposed opposite a domed end of the first stem component; and
      a second stem component sized and configured to be installed in the intramedullary path, the second stem component including a first internal feature including at least two flats disposed at a second internally threaded female end that is disposed opposite a first externally threaded male end, a second external feature including at least two flats is disposed at the second internally threaded female end;
   a tibial tray configured to be attached to the prosthesis stem, the tibial tray defining a channel extending in an anterior-posterior direction between a pair of opposed rails, a notch is defined in the tibial tray between the pair of opposed rails; and
   an artificial joint surface sized and configured to be received within the channel of the tibial tray, an upper surface of the artificial joint surface including a decent that is sized and configured to be received with the notch,
   wherein the first external feature is configured to be engaged by a tool to prevent rotation of the first stem component when the second stem component is rotated in response to being driven by a driving tool that engages the first internal feature to connect the first and second stem components to each other in situ.

2. The prosthesis of claim 1, wherein the prosthesis stem further includes:
   a third stem component sized and configured to be installed in the intramedullary path and connected to at least one of the first and second stem components in situ.

3. The prosthesis of claim 1, wherein the first externally threaded male end of the second stem component is configured to engage the first internally threaded female end of the first stem component.

4. The prosthesis of claim 1, wherein the artificial joint surface is configured to be attached to at least one of the first and second stem components.

5. The prosthesis of claim 4, wherein the artificial joint surface includes one of a concave or a convex joint surface.

6. The prosthesis of claim 1, wherein the prosthesis stem is sized and configured to be disposed in a tibia.

7. The prosthesis of claim 1, wherein the prosthesis stem is sized and configured to be disposed in a talus.

8. The prosthesis of claim 1, wherein the first and second internal features are internal hex features, and the first and second external features are external hex features.

9. The prosthesis of claim 1, wherein the first external feature has a cross-sectional dimension that is smaller than a largest cross-sectional dimension of the first prosthesis stem component, and the second external feature has a cross-sectional dimension that is smaller than a largest cross-sectional dimension of the second prosthesis stem component.

10. An ankle prosthesis, comprising:
a tibial prosthesis including:
a tibial stem sized and configured to be disposed in an intramedullary path formed in a tibia, the tibial stem including first and second stem components, the first stem component having a first external feature including at least two flats disposed at a first internally threaded female end, the second stem component including a first internal hex feature, the at least two flats of the first external feature includes is configured to be engaged by a tool to prevent rotation of the first stem component when the second stem component is rotated in response to being driven by a driving tool that engages the first internal hex feature to connect the first and second stem components;
a platform configured to be attached to the tibial stem and defining a channel that extends in an anterior-posterior direction between a pair of opposed side rails; and
a first artificial joint surface configured to slide into engagement with the channel of the platform, the first artificial joint surface including a detent on an upper surface that is sized and configured to be received within a notch defined by the platform between the side rails;
a talar prosthesis including:
a talar stem sized and configured to be disposed in an intramedullary path formed in a talus; and
a second artificial joint surface configured to be attached to the talar stem and to articulate with the first artificial joint surface,
wherein a plurality of tibial stem components including the first and second stem components are configured to be connected in situ.

11. The prosthesis of claim 10, wherein the first and second artificial joint surfaces have complementary saddle-shapes.

12. The prosthesis of claim 10, wherein the talar stem includes a plurality of stem components.

13. The prosthesis of claim 10, wherein the talar stem is configured to extend from the talus into a calcaneus.

14. A method, comprising:
inserting a first stem component of a prosthesis stem into an intramedullary path, the first stem component including a first internally threaded female end that is disposed opposite a domed end of the first stem component, the internally threaded female end including a first external feature including at least a pair of flats;
inserting a second stem component of the prosthesis into the intramedullary path, the second stem component including a first externally threaded male end configured to engage the internally threaded female end of the first stem component, a second pair of flats is disposed at a second internally threaded female end of the second stem component that is disposed opposite the first externally threaded male end of the second stem component;
connecting the first and second stem components in situ by engaging a first internal feature of the second stem component located within the second internally threaded female end with a driving tool to rotate the second stem component while the pair of flats of the first external feature of the first stem component is engaged with a second tool to prevent rotation of the first stem component as the second stem component is being rotated;
connecting a tibial tray to the prosthesis stem, the tibial tray defining a channel extending in an anterior-posterior direction between a pair of opposed rails, a notch is defined in the tibial tray between the pair of opposed rails; and
inserting an artificial joint surface into the channel of the tibial tray until a detent extending from an upper surface of the artificial joint surface is received with the notch.

15. The method of claim 14, wherein the intramedullary path is formed in a tibia.

* * * * *